(12) United States Patent
Liu et al.

(10) Patent No.: US 9,955,886 B2
(45) Date of Patent: May 1, 2018

(54) FOCUSED RECORDING AND STIMULATION ELECTRODE ARRAY

(71) Applicant: THE REGENTS OF THE UNIVERSITY OF CALIFORNIA, Oakland, CA (US)

(72) Inventors: Wentai Liu, Los Angeles, CA (US); Chih-Wei Chang, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days. days.

(21) Appl. No.: 14/990,874

(22) Filed: Jan. 8, 2016

(65) Prior Publication Data

US 2016/0192854 A1    Jul. 7, 2016

Related U.S. Application Data

(63) Continuation of application No. PCT/US2014/046927, filed on Jul. 16, 2014.
(Continued)

(51) Int. Cl.
*A61B 5/04* (2006.01)
*A61B 5/0408* (2006.01)
(Continued)

(52) U.S. Cl.
CPC ............ *A61B 5/04085* (2013.01); *A61B 5/04* (2013.01); *A61B 5/0478* (2013.01);
(Continued)

(58) Field of Classification Search
CPC ...... A61B 5/04085; A61B 5/04; A61B 5/0478; A61B 5/0492; A61B 2562/046; A61N 1/0456
See application file for complete search history.

(56) References Cited

U.S. PATENT DOCUMENTS

2009/0082688 A1    3/2009 Wagner
2011/0046506 A1    2/2011 Urand et al.
(Continued)

FOREIGN PATENT DOCUMENTS

WO    2012-046237 A2    4/2012
WO    2012-154701 A1    11/2012

OTHER PUBLICATIONS

B. Wodlinger, A. D. Degenhart, J. L. Collinger, E. C. Tyler-Kabara, and W. Wei, "The impact of electrode characteristics on electrocorticography (ECoG)," in Engineering in Medicine and Biology Society,EMBC, 2011 Annual International Conference of the IEEE, 2011, pp. 3083-3086.
(Continued)

*Primary Examiner* — Paula J Stice
(74) *Attorney, Agent, or Firm* — O'Banion & Ritchey LLP; John P. O'Banion

(57) ABSTRACT

Neural signal recording apparatus and method is described, in which a micro electrode array is utilized for performing a weighted matrix as a moving window providing superpositioning of electrode signals. A voltage distribution across the electrode array is determined as a Laplacian. The apparatus and method can be utilized in a variety of electrode sensing applications involving registering neural activity, and for electrode stimulation applications, or combinations thereof.

25 Claims, 20 Drawing Sheets

Related U.S. Application Data

(60) Provisional application No. 61/847,441, filed on Jul. 17, 2013.

(51) Int. Cl.
*A61B 5/0478* (2006.01)
*A61N 1/04* (2006.01)
*A61N 1/36* (2006.01)
*A61B 5/0492* (2006.01)

(52) U.S. Cl.
CPC .......... *A61B 5/0492* (2013.01); *A61N 1/0456* (2013.01); *A61N 1/0476* (2013.01); *A61N 1/36014* (2013.01); *A61B 2562/046* (2013.01)

(56) References Cited

U.S. PATENT DOCUMENTS

| | | | |
|---|---|---|---|
| 2011/0054583 A1* | 3/2011 | Litt | A61B 5/0031 607/116 |
| 2013/0060125 A1 | 3/2013 | Zeman et al. | |

OTHER PUBLICATIONS

S. Kellis, B. Greger, S. Hanrahan, P. House, and R. Brown, "Sensing millimeter-scale dynamics in cortical surface potentials for neural prosthetics," in Sensors, 2011 IEEE, 2011, pp. 1823-1826.

D. Farina and C. Cescon, "Concentric-ring electrode systems for noninvasive detection of single motor unit activity," Biomedical Engineering, IEEE Transactions on, vol. 48, pp. 1326-1334, 2001.

O. Makeyev, X. Liu, Fl Luna-Munguia, G. Rogel-Salazar, S. Mucio-Ramirez, Y. Liu, Y. L. Sun, S. M. Kay, and W. G. Besio, "Toward a Noninvasive Automatic Seizure Control System in Rats With Transcranial Focal Stimulations via Tripolar Concentric Ring Electrodes," Ieee Transactions on Neural Systems and Rehabilitation Engineering, vol. 20, pp. 422-431, Jul. 2012.

J. D. Wiley and J. G. Webster, "Analysis and Control of the Current Distribution Under Circular Dispersive Electrodes," Ieee Transactions on Biomedical Engineering, vol. 29, pp. 381-385, 1982.

K. Koka and W. G. Besio, "Improvement of spatial selectivity and decrease of mutual information of tri-polar concentric ring electrodes," Journal of Neuroscience Methods, vol. 165, pp. 216-222, Sep. 30, 2007.

W. Besio and T. Chen, "Tripolar Laplacian electrocardiogram and moment of activation isochronal mapping," Physiological Measurement, vol. 28, pp. 515-529, May 2007.

G. Prats-Boluda, J. Garcia-Casado, J. L. Martinez-de-Juan, and Y. Ye-Lin, "Active concentric ring electrode for non-invasive detection of intestinal myoelectric signals," Medical Engineering & Physics, vol. 33, pp. 446-455, May 2011.

G. Prats-Boluda, Y. Ye-Lin, E. Garcia-Breijo, J. Ibanez, and J. Garcia-Casado, "Active flexible concentric ring electrode for non-invasive surface bioelectrical recordings," Measurement Science & Technology, vol. 23, Dec. 2012.

W. G. Besio, S. M. Kay, and X. Liu, "An optimal spatial filtering electrode for brain computer interface," 2009 31st Annual International Conference of the IEEE Engineering in Medicine and Biology Society. EMBC 2009, pp. 3138-3141, Jan. 2009.

M. W. Slutzky, L. R. Jordan, T. Krieg, M. Chen, D. J. Mogul, and L. E. Miller, "Optimal spacing of surface electrode arrays for brain-machine interface applications," Journal of Neural Engineering, vol. 7, Apr. 2010.

D. Farina and R. Merletti, "A novel approach for precise simulation of the EMG signal detected by surface electrodes," Ieee Transactions on Biomedical Engineering, vol. 48, pp. 637-646, Jun. 2001.

J. D. Quartararo and E. A. Clancy, "Spatially selective filter design for high-resolution EMG arrays," 2007 3rd International IEEE/EMBS Conference on Neural Engineering, pp. 4 pp.-4 pp., Jan. 2007.

C. DisselhorstKlug, J. Silny, and G. Rau, "Improvement of spatial resolution in surface-EMG: A theoretical and experimental comparison of different spatial filters," Ieee Transactions on Biomedical Engineering, vol. 44, pp. 567-574, Jul. 1997.

W. Besio, R. Aakula, K. Koka, and W. Dai, "Development of a tri-polar concentric ring electrode for acquiring accurate Laplacian body surface potentials," Annals of Biomedical Engineering, vol. 34, pp. 426-435, Mar. 2006.

G. Besio, K. Koka, R. Aakula, and D. Weizhong, "Tri-polar concentric ring electrode development for Laplacian electroencephalography," Ieee Transactions on Biomedical Engineering, vol. 53, pp. 926-933, May 2006.

H. Bin and R. J. Cohen, "Body surface Laplacian ECG mapping," Biomedical Engineering, IEEE Transactions on, vol. 39, pp. 1179-1191, 1992.

C.-W. Chang and J.-C. Chiou, "Development of a Three Dimensional Neural Sensing Device by a Stacking Method," Sensors, vol. 10, pp. 4238-4252, May 2010.

Ad-Tech Medical Instrument Corporation, "Subdural Electrodes", downloaded from http://www.adtechmedical.com/ on Jan. 8, 2016, copyright 1985-2016 AdTech Medical Instrument Corporation, pp. 1-3.

Korean Intellectual Property Office (KIPO), International Search Report and Written Opinion, PCT/US2014/046927, dated Oct. 29, 2014, pp. 1-13, with claims searched, pp. 14-21, corresponding to the application filed herewith.

\* cited by examiner

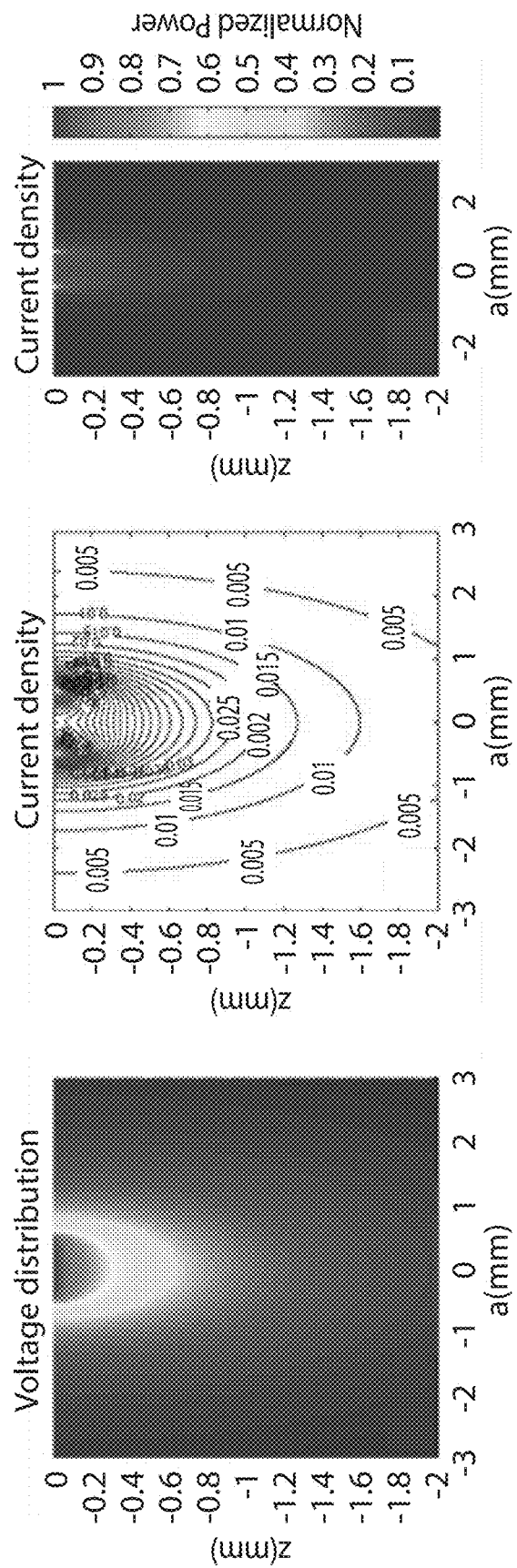

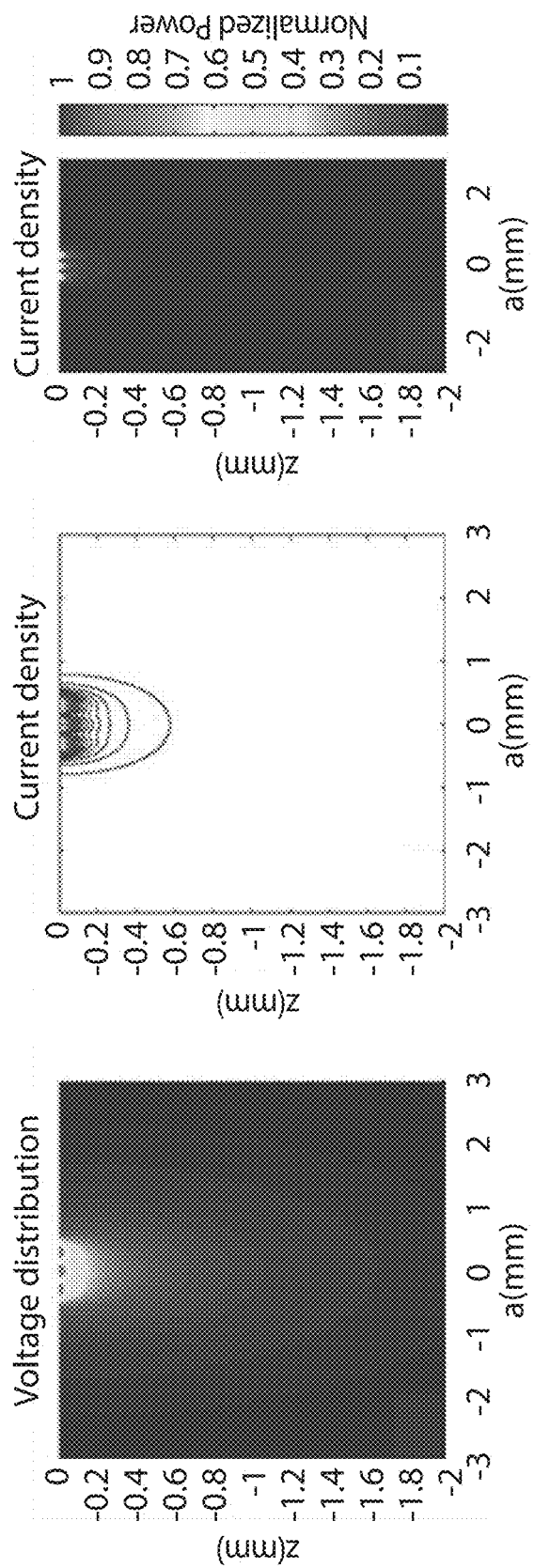

FOCUSED RECORDING AND STIMULATION ELECTRODE ARRAY

CROSS-REFERENCE TO RELATED APPLICATIONS

This application is a 35 U.S.C. § 111(a) continuation of PCT international application number PCT/US2014/046927 filed on Jul. 16, 2014, incorporated herein by reference in its entirety, which claims priority to, and the benefit of, U.S. provisional patent application Ser. No. 61/847,441 filed on Jul. 17, 2013, incorporated herein by reference in its entirety. Priority is claimed to each of the foregoing applications.

The above-referenced PCT international application was published as PCT International Publication No. WO 2015/009877 on Jan. 22, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND

1. Technological Field

This invention pertains generally to neural signal recording and stimulation, and more particularly to a micro electrode apparatus and method which uses a moving window and optimized weighting matrix.

2. Background Discussion

Spatial resolution has its limits when using traditional disk electrodes for different neural signal recording (i.e., Electroencephalography (EEG), electrocorticography (ECoG)). The spatial resolution of the recording electrodes depends on the electrode size and the properties of the mediate tissue located between the electrodes and the neural signal location.

Several methods have been proposed for creating high-resolution electrode systems by directly employing dense electrode arrays for large channel-count neural sensing. These proposed approaches typically suffer from high mutual signal levels which arise in adjacent electrodes due to low spatial resolution. One such method uses spatial filters. However, the use of spatial filters are not configured to provide optimization under different neural recording conditions, resolution, combinations of electrode size and pitch between electrodes, and combinations thereof. Another such method using dense electrode arrays utilizes surface Laplacian ring electrodes providing concentric ring electrodes with weightings based on Laplacian or optimal calculations to improve spatial resolution in certain multiple ring areas. However, use of a ring structure has limited scalability.

Accordingly, a need exists for providing high resolution neural sensing and stimulation.

BRIEF SUMMARY

A micro electrode array apparatus and method is presented which achieves high spatial resolution in sensing (registration and/or recording) and stimulation. An optimized weighting matrix is performed within a moving window in response to superpositioning of electrode signals. The weighting matrix can be configured for two or three dimensions. Use of the micro electrode array provides adjustable spatial resolution of each electrode for neural recording.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 3:
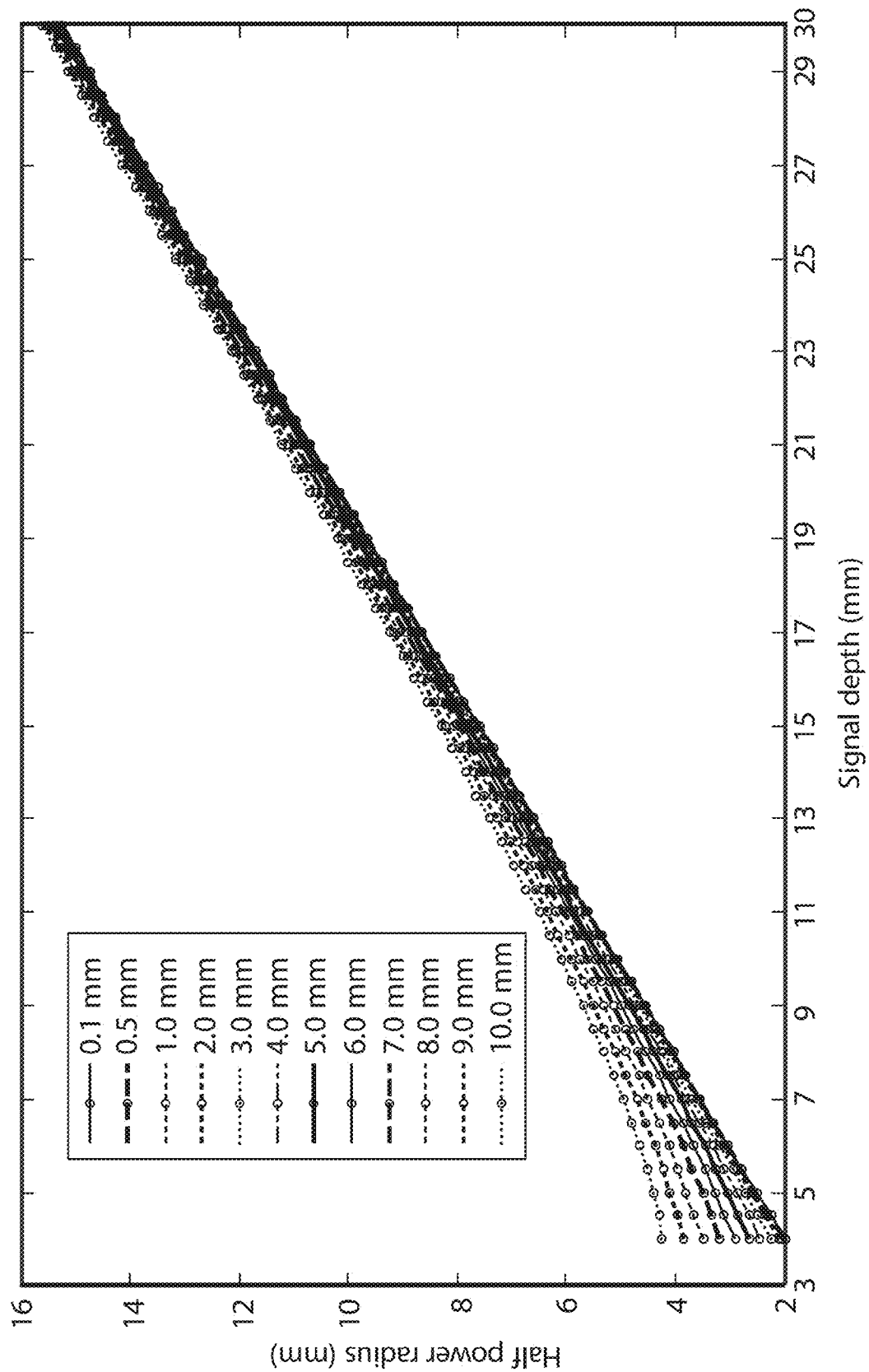

FIG. 3 a plot of half power radius for various electrode size and signal source depth.

Figure 4A:
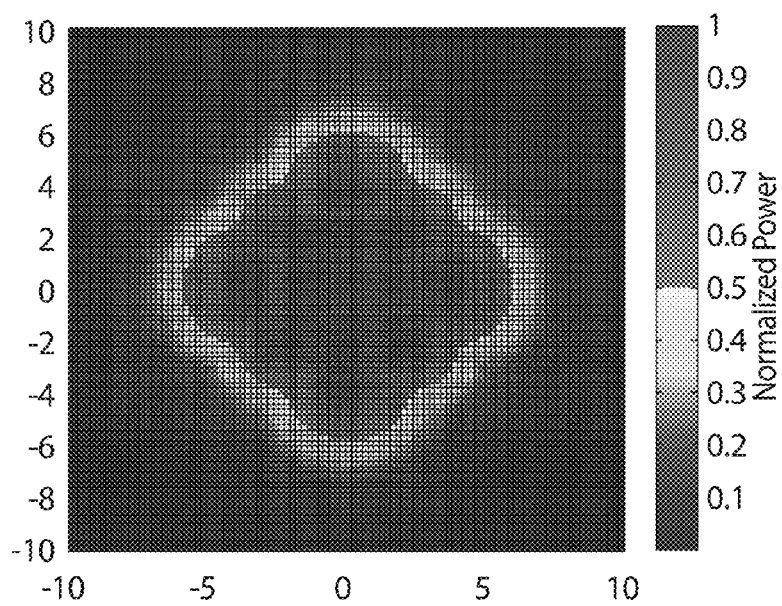
Figure 4B:
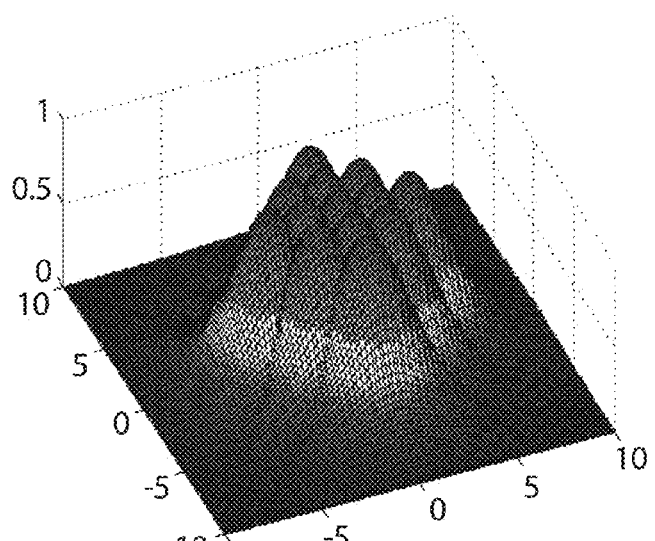

FIG. 4A and FIG. 4B are 2D and 3D plots of normalized power distribution for a 1.0 mm electrode at a 1.8 mm electrode array pitch.

Figure 5:
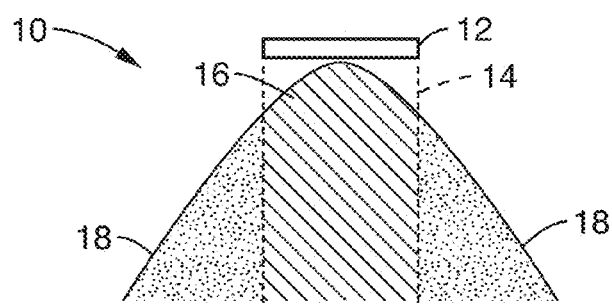

FIG. 5 is a diagram defining signal power in relation to noise power for determining an optimal weighting matrix according to an embodiment of the disclosed technology.

Figure 6A:
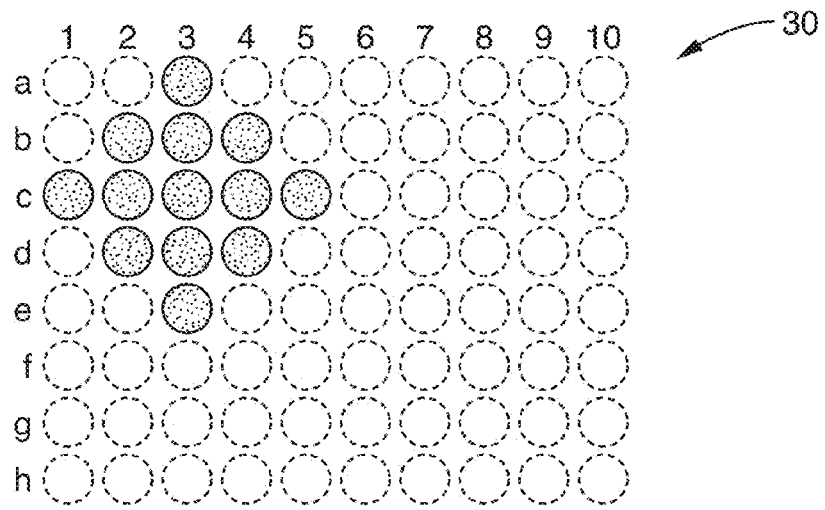
Figure 6B:
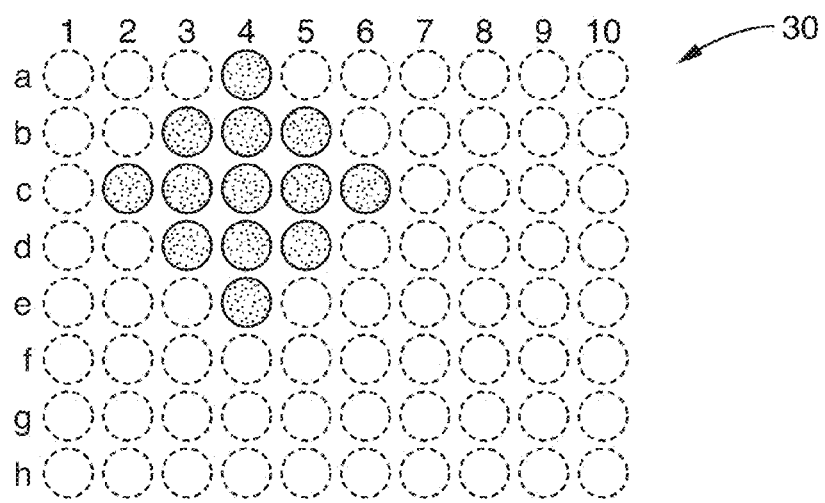
Figure 6C:
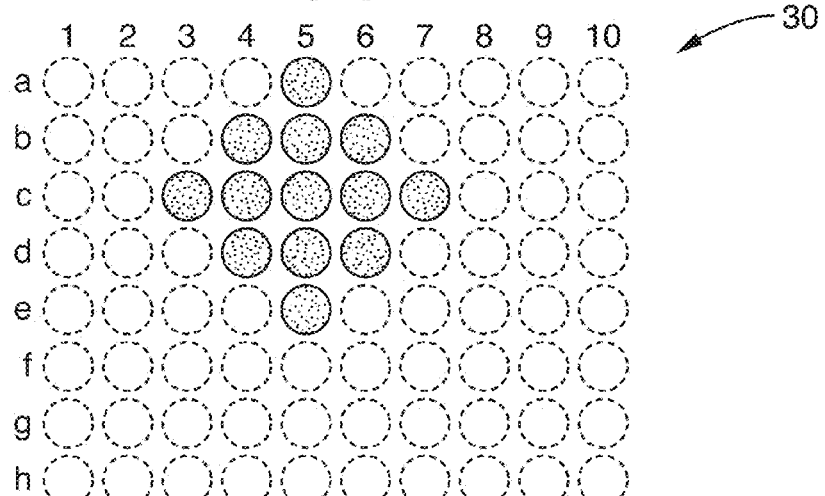

FIG. 6A through FIG. 6C are diagrams of a moving window weighted matrix electrode array according to an embodiment of the disclosed technology.

Figure 7A:
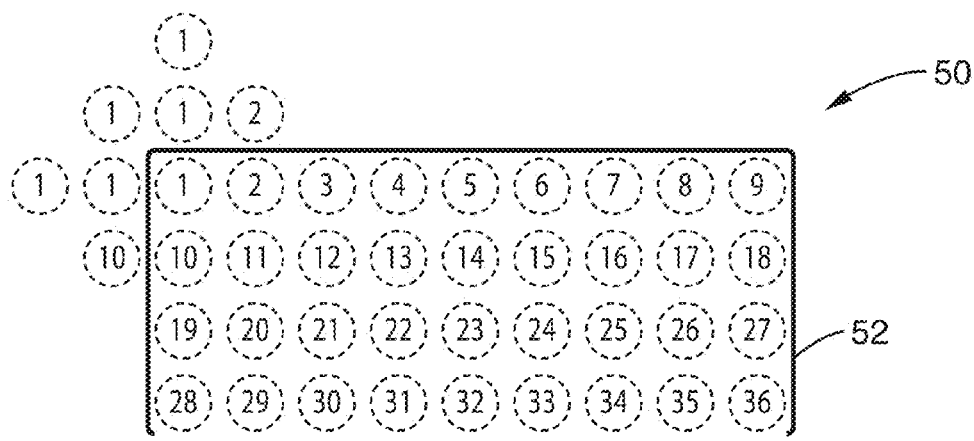
Figure 7B:
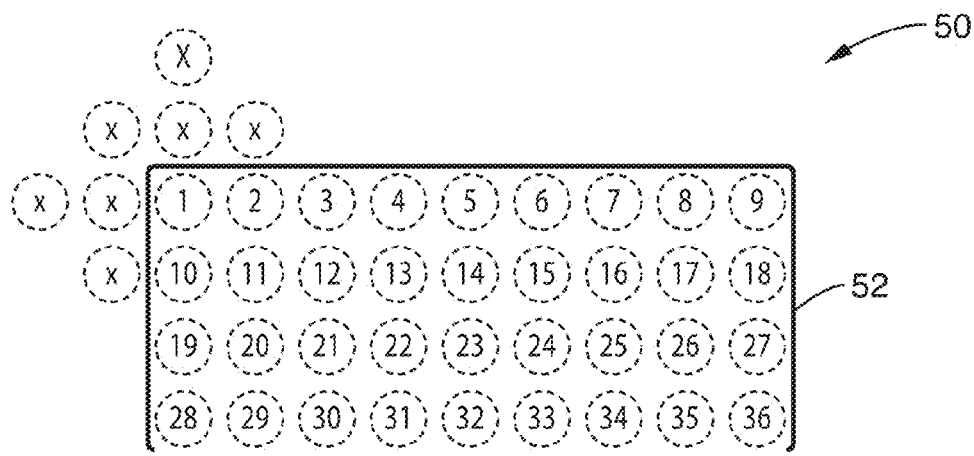
Figure 7C:
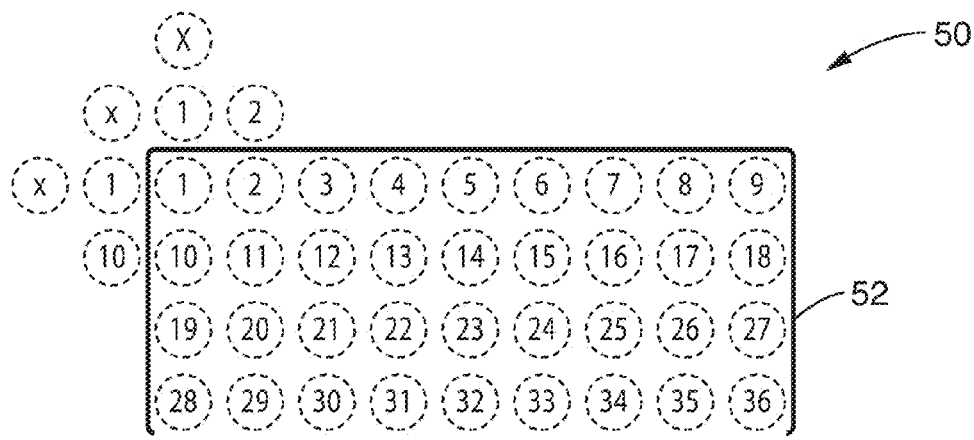

FIG. 7A through FIG. 7C are diagrams of a weighting matrix operating on the electrode array edge according to an embodiment of the disclosed technology.

Figure 8A:
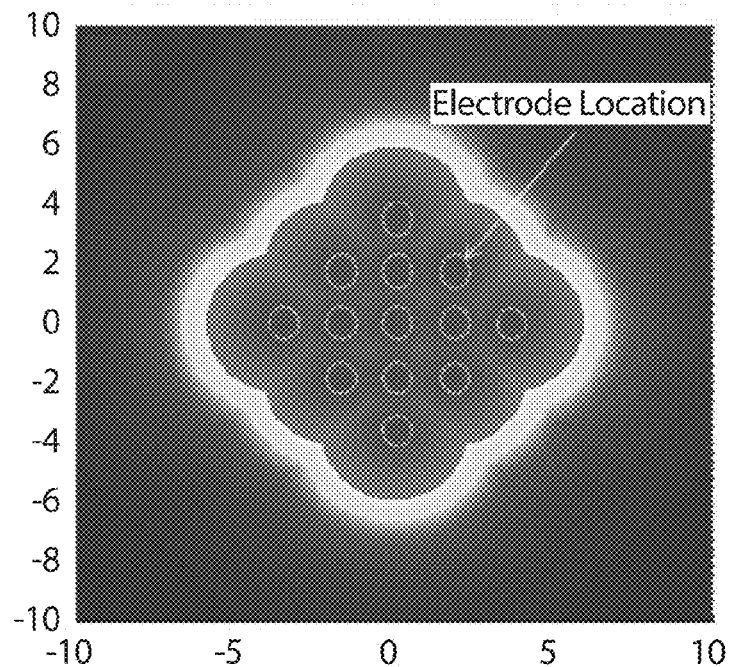
Figure 8B:
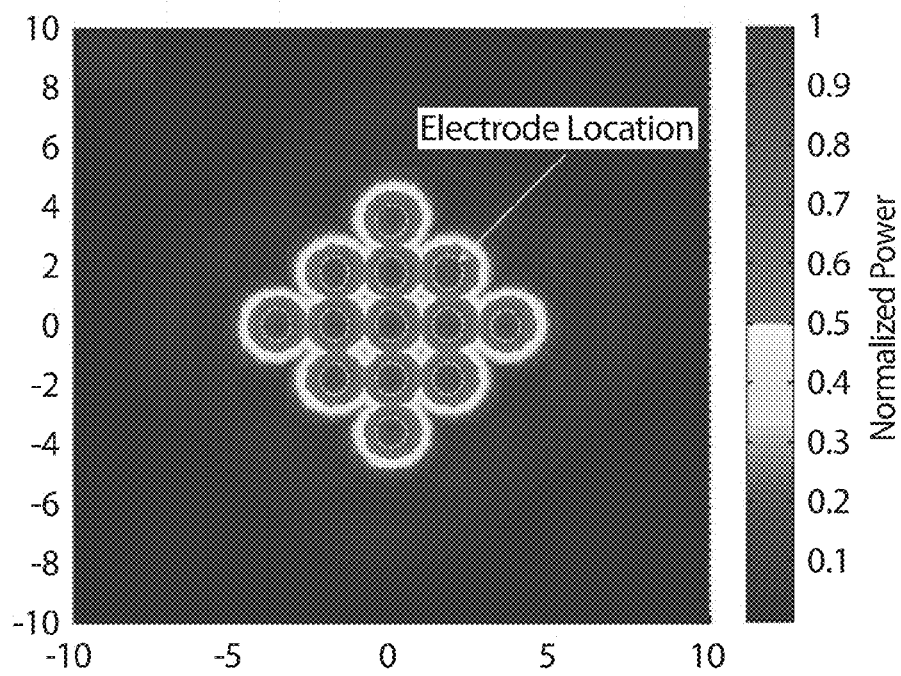

FIG. 8A and FIG. 8B are 2D plots of normalized power for a first configuration of electrode matrix seen before (FIG. 8A), and after (FIG. 8B), applying an optimal weighting matrix according to an embodiment of the disclosed technology.

Figure 9A:
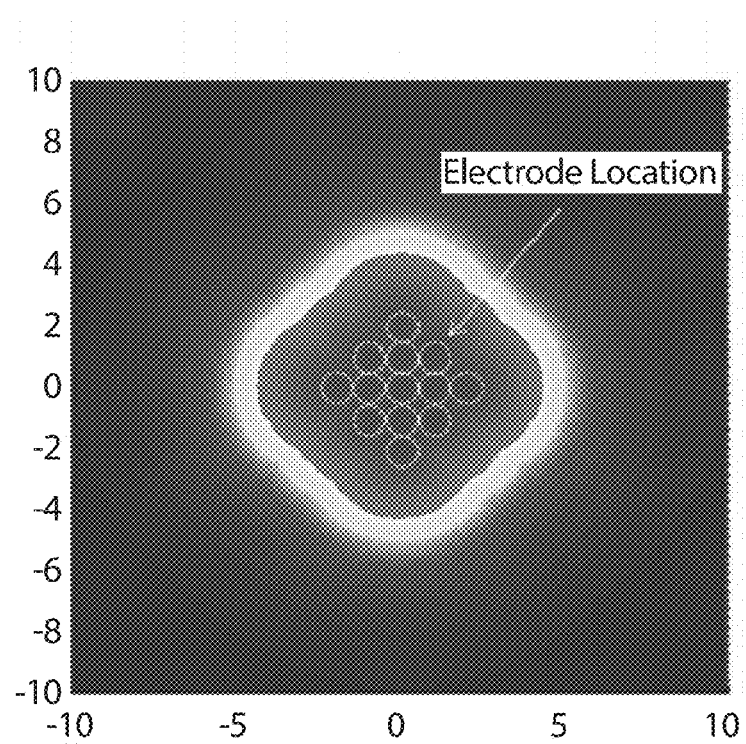
Figure 9B:
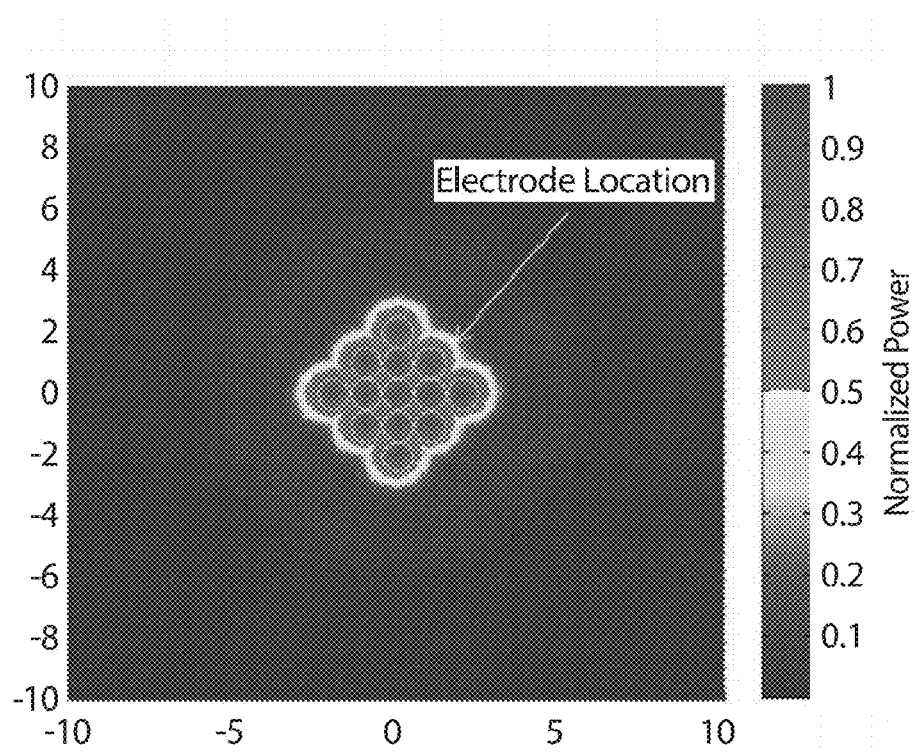

FIG. 9A and FIG. 9B are 2D plots of normalized power for a second configuration of electrode matrix before (FIG. 9A), and after (FIG. 9B) applying an optimal weighting matrix according to an embodiment of the disclosed technology.

Figure 10:
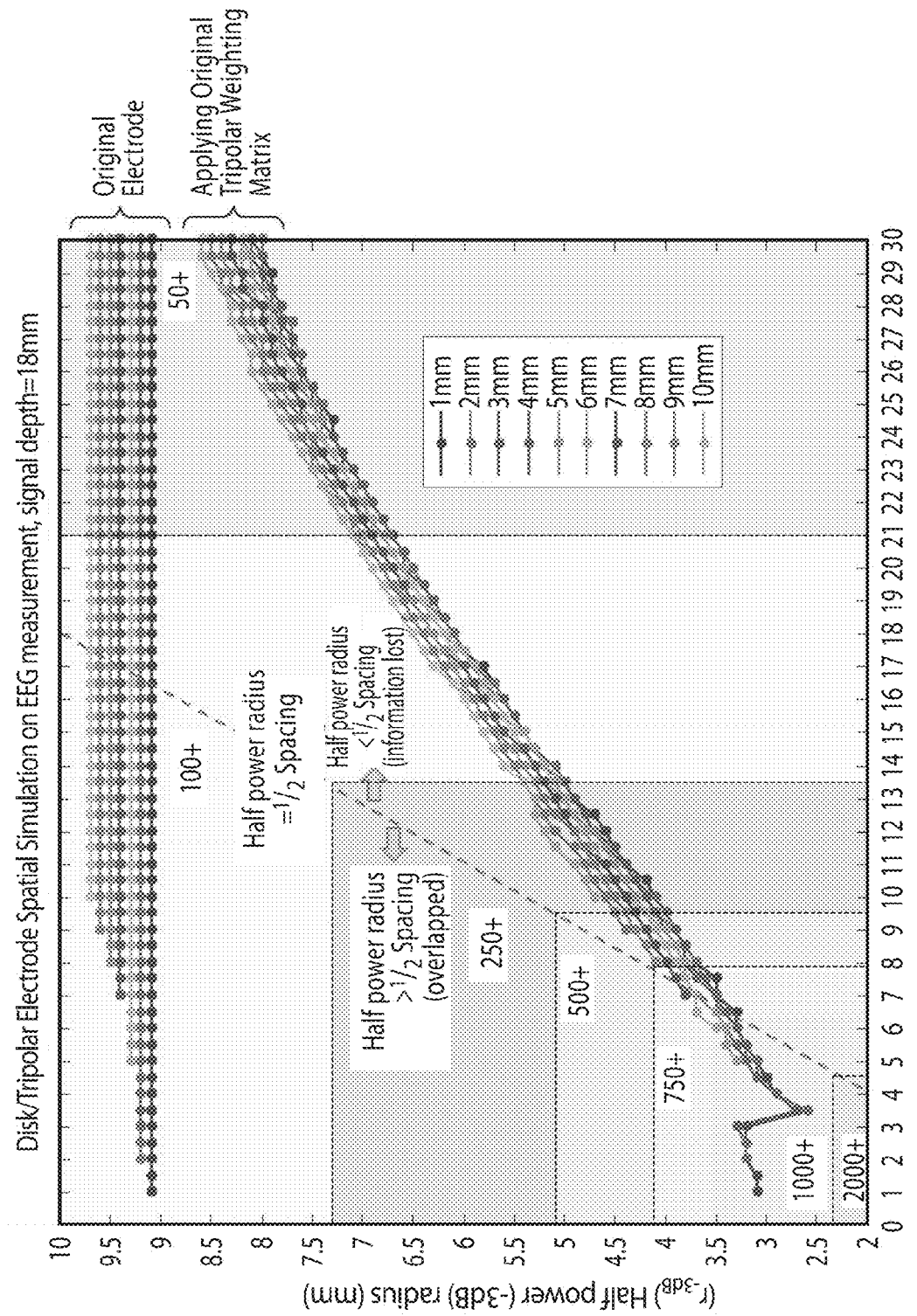

FIG. 10 is a plot of half-power radius for electrode spatial simulation on an EEG measurement comparing a tripolar weighting matrix according to an embodiment of the disclosed technology with the original electrode.

Figure 11:
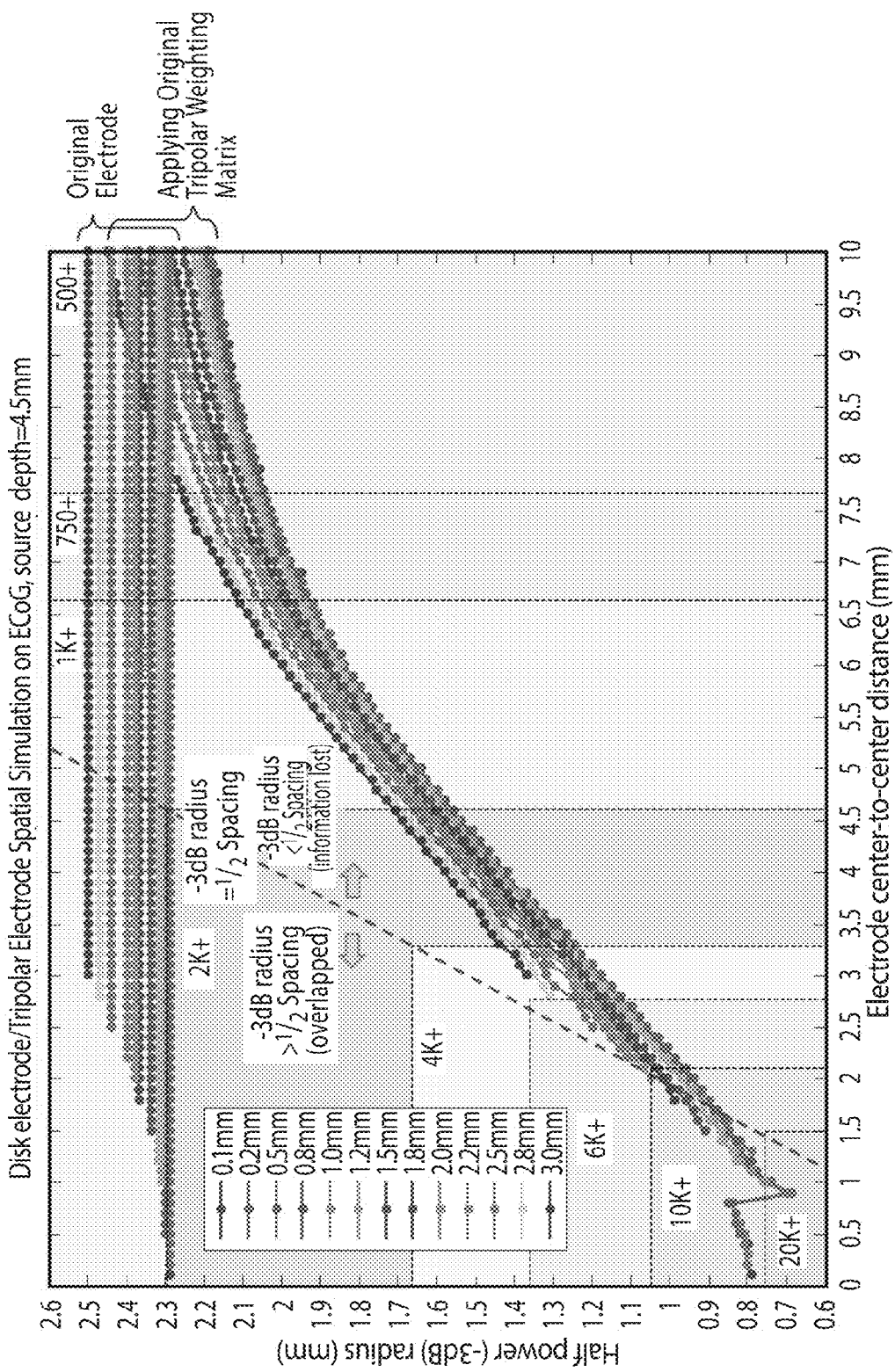

FIG. 11 is a plot of half-power radius for electrode spatial simulation on an ECoG measurement comparing a tripolar weighting matrix according to an embodiment of the disclosed technology with the original electrode.

Figure 12:
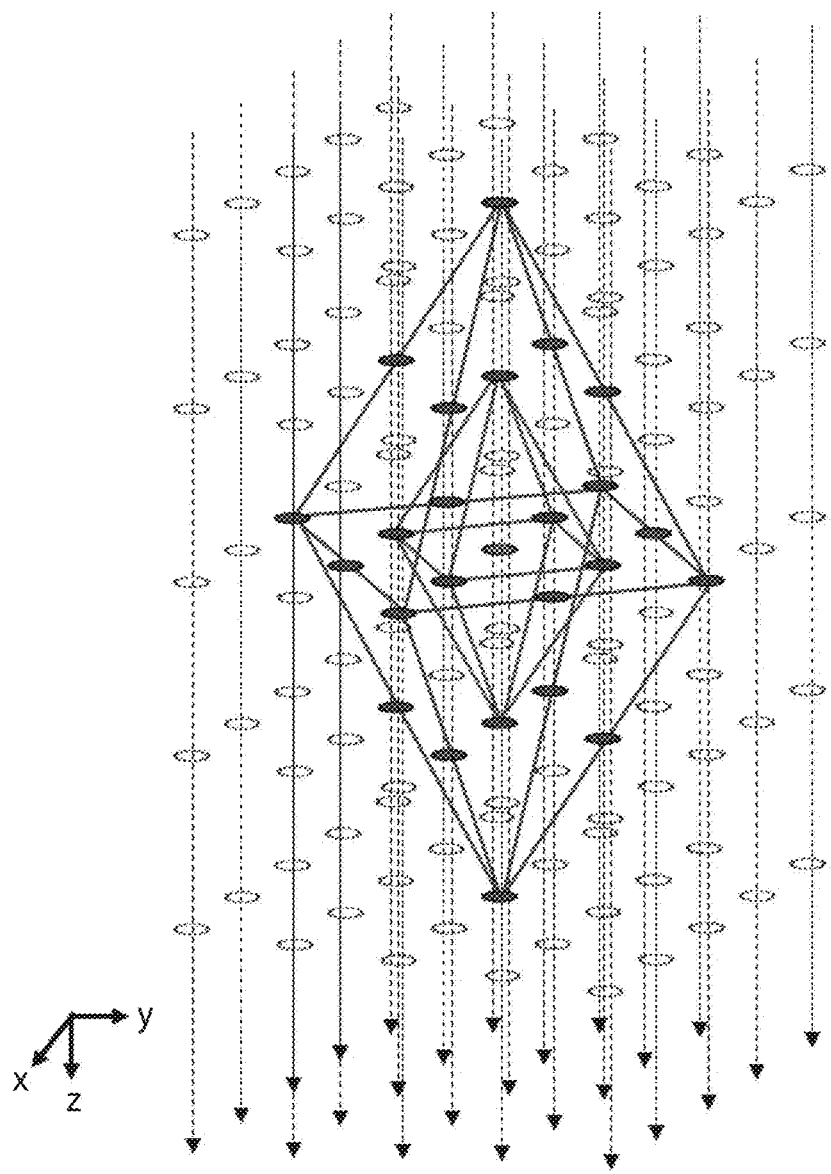

FIG. 12 is a diagram of a 3D tripolar weighting matrix for focused three dimensional recording according to an embodiment of the disclosed technology.

Figure 13:
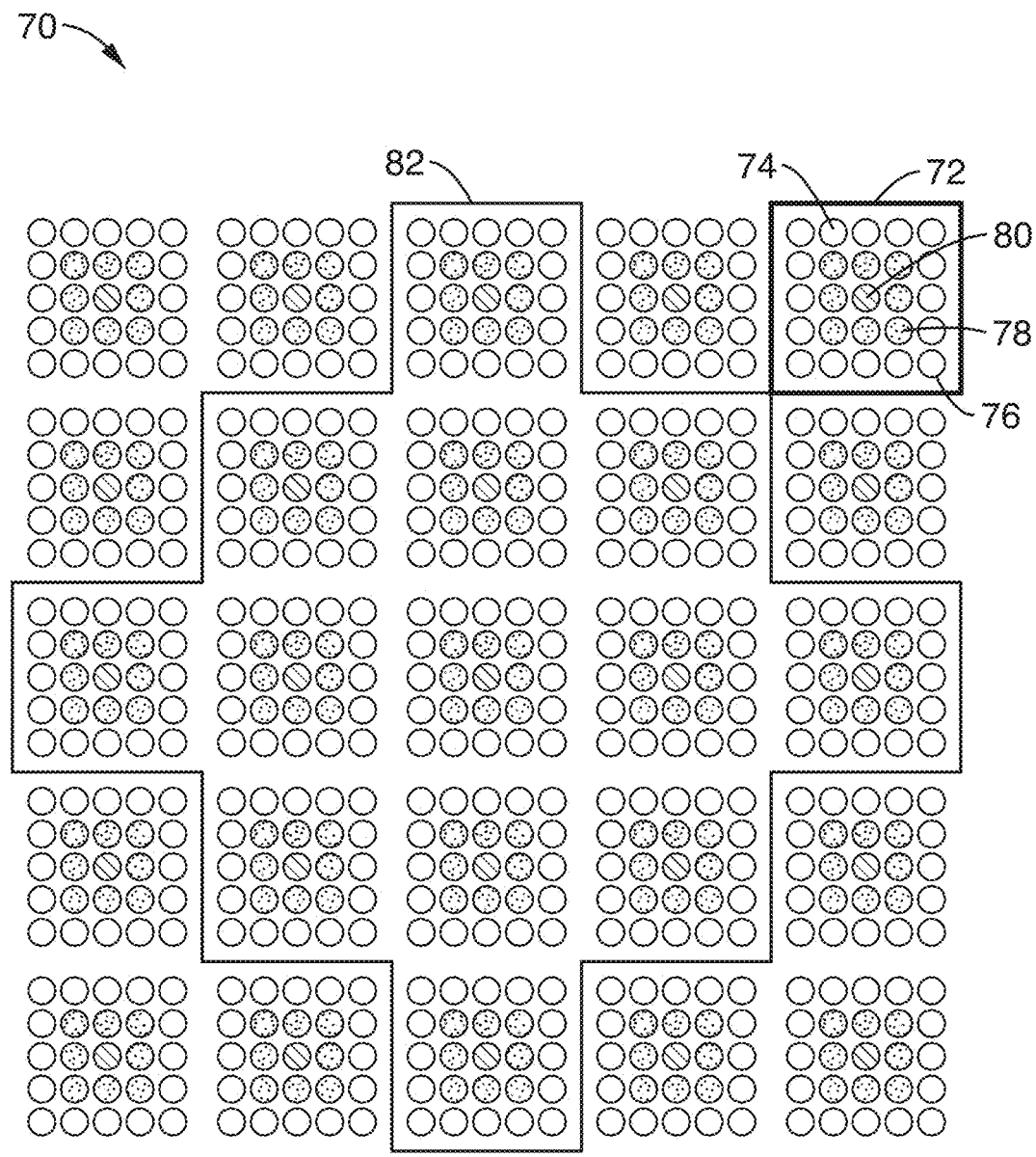

FIG. 13 is a diagram of a combined focused recording and stimulation electrode embodiment according to the disclosed technology, showing division of the original disk electrodes into n by n small electrodes.

FIG. 14A through FIG. 14C are distributions and plots of voltage distribution and current density determined according to an embodiment of the disclosed technology.

Figures 15A, 15B, 15C:
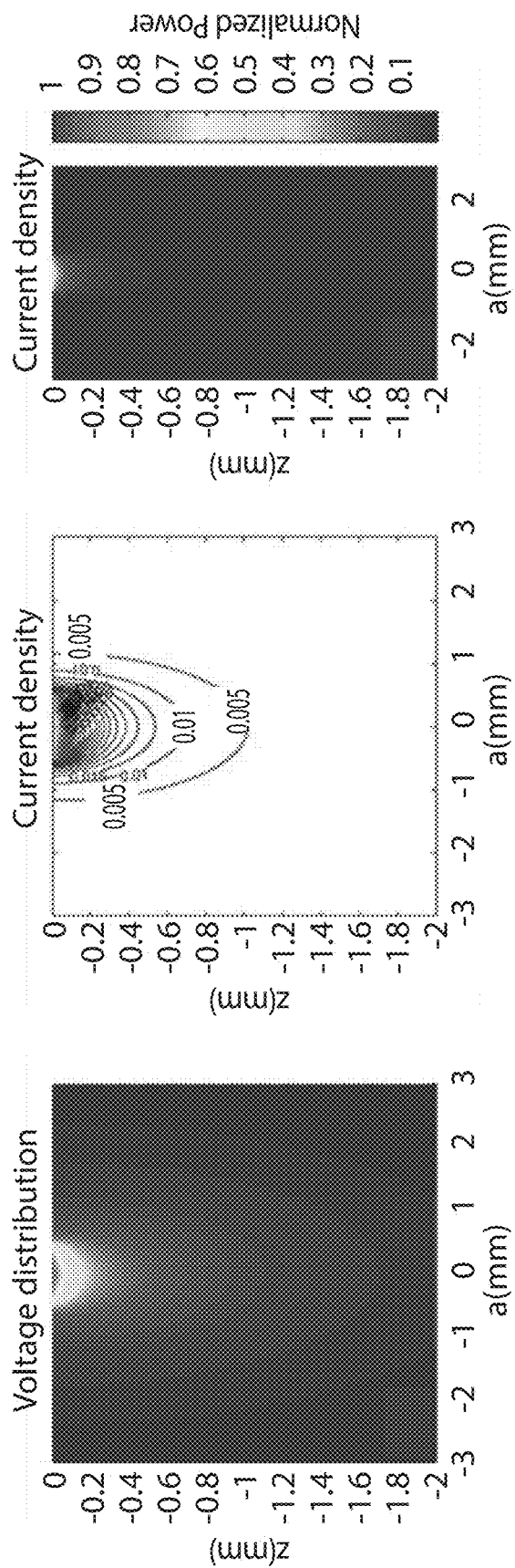

FIG. 15A through FIG. 15C are distributions and plots of voltage distribution and current density determined according to an embodiment of the disclosed technology, shown providing a first current density distribution.

Figure 16C:
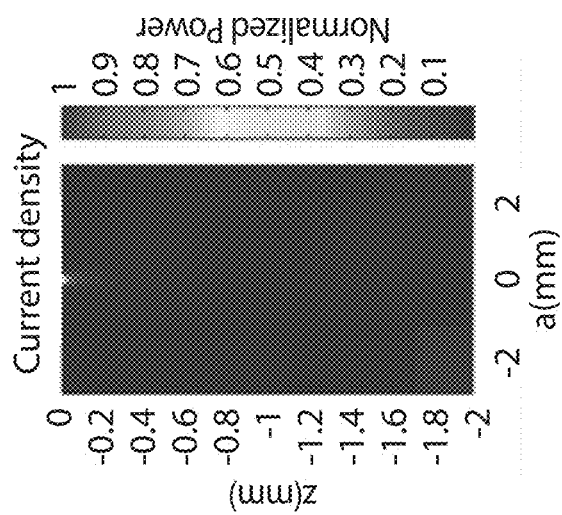
Figure 16B:
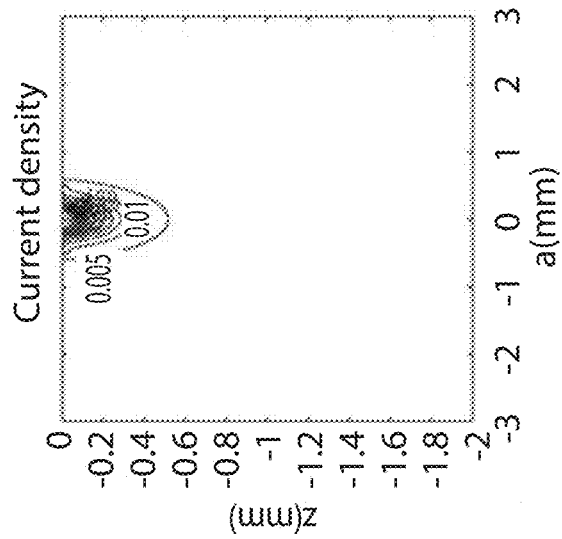
Figure 16A:
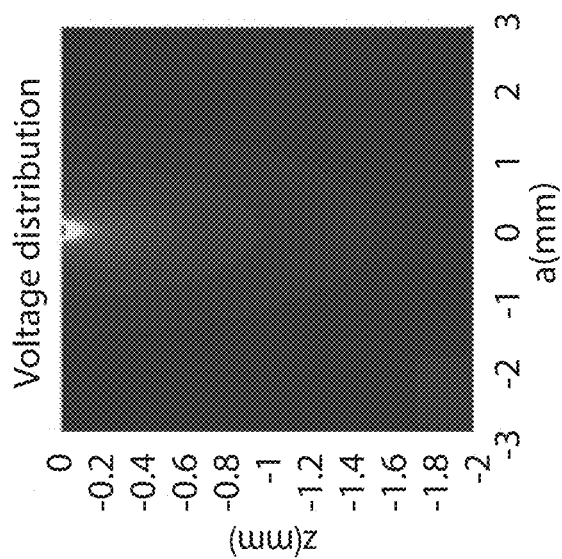

FIG. 16A through FIG. 16C are distributions and plots of voltage distribution and current density determined according to an embodiment of the disclosed technology, shown for providing a second current density distribution.

FIG. 17A through FIG. 17C are distributions and plots of voltage distribution and current density determined according to an embodiment of the disclosed technology, shown for providing a third current density distribution having focused tri-spots in the current density distribution.

Figure 18C:
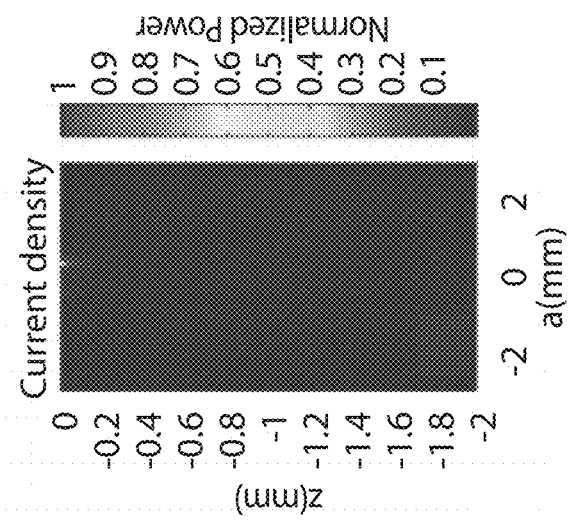
Figure 18B:
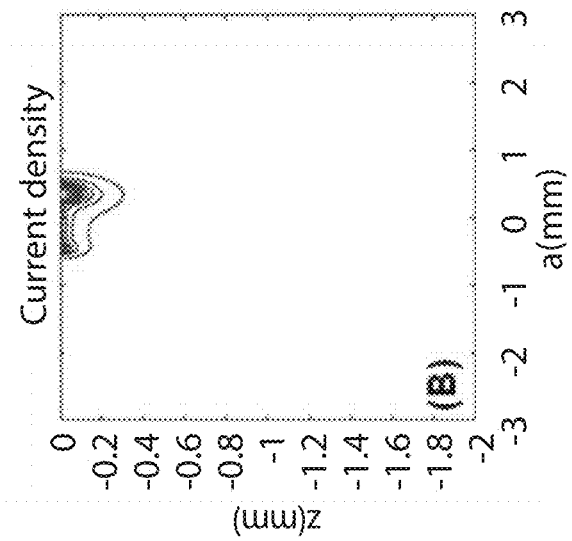
Figure 18A:
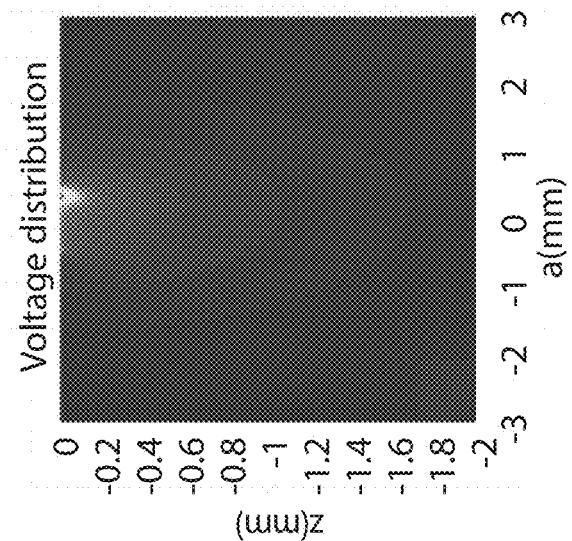

FIG. 18A through FIG. 18C are distributions and plots of voltage distribution and current density determined according to an embodiment of the disclosed technology, shown for providing an arbitrary (selectable) controlled single-spot current density distribution.

Figure 19:
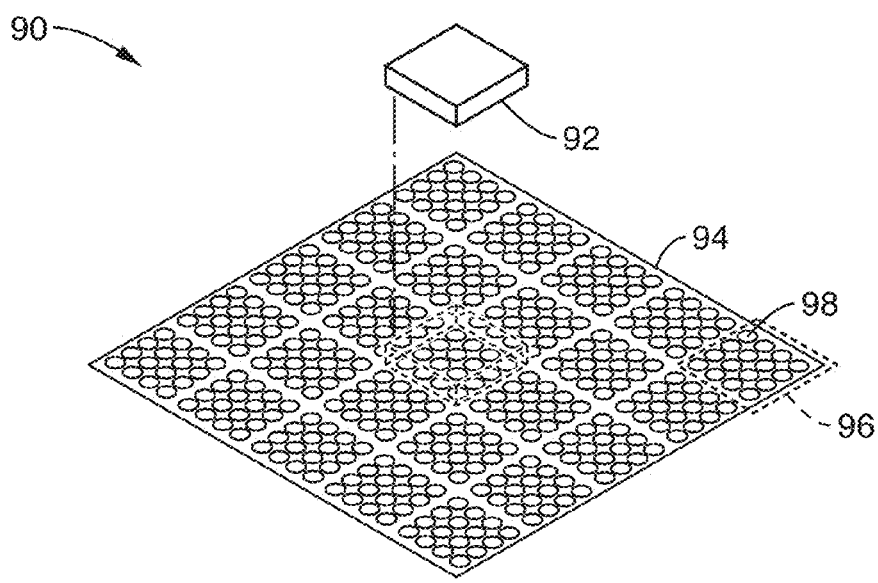

FIG. 19 is a pictorial diagram of an electrode array integrated according to an embodiment of the disclosed technology, showing active circuits for recording and stimulation bonded to an array substrate.

Figure 20:
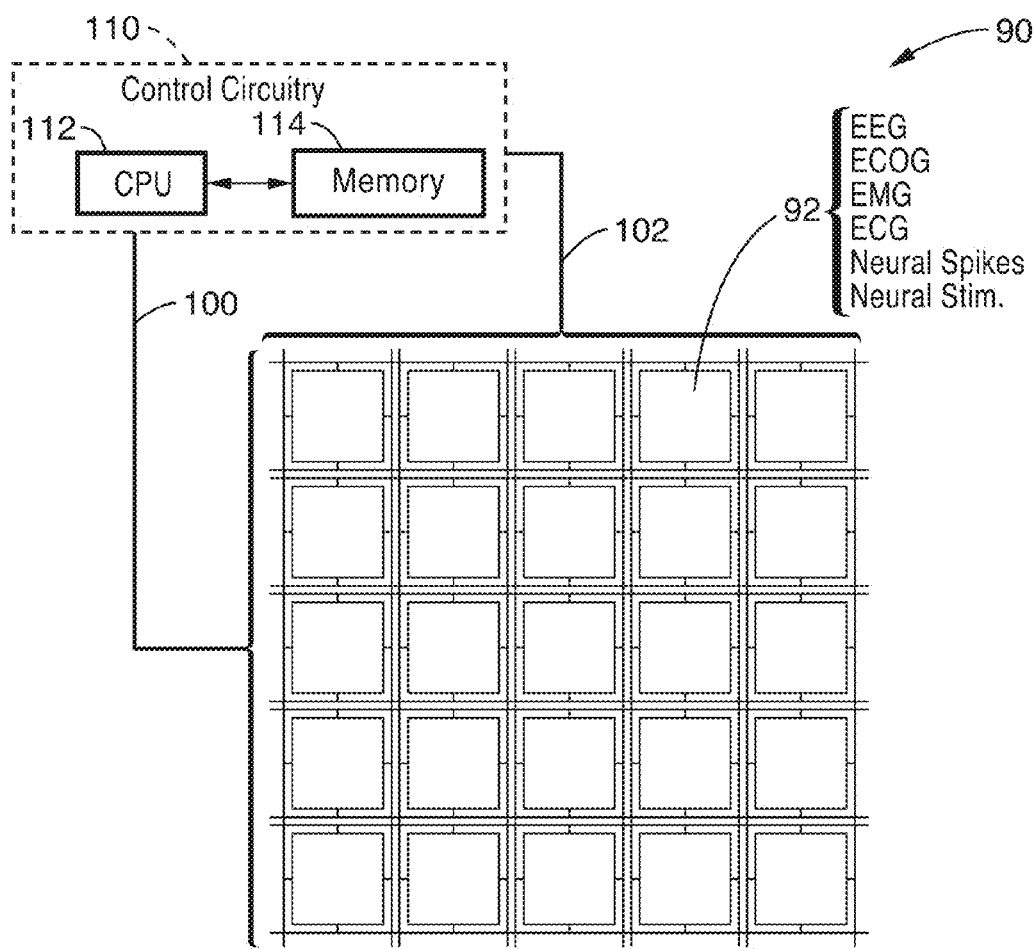

FIG. 20 is a top view of an electrode array integrated according to an embodiment of the disclosed technology, showing data and control signal routing about the periphery of an array of active sensing/stimulation circuits as seen in FIG. 19.

Figure 21:
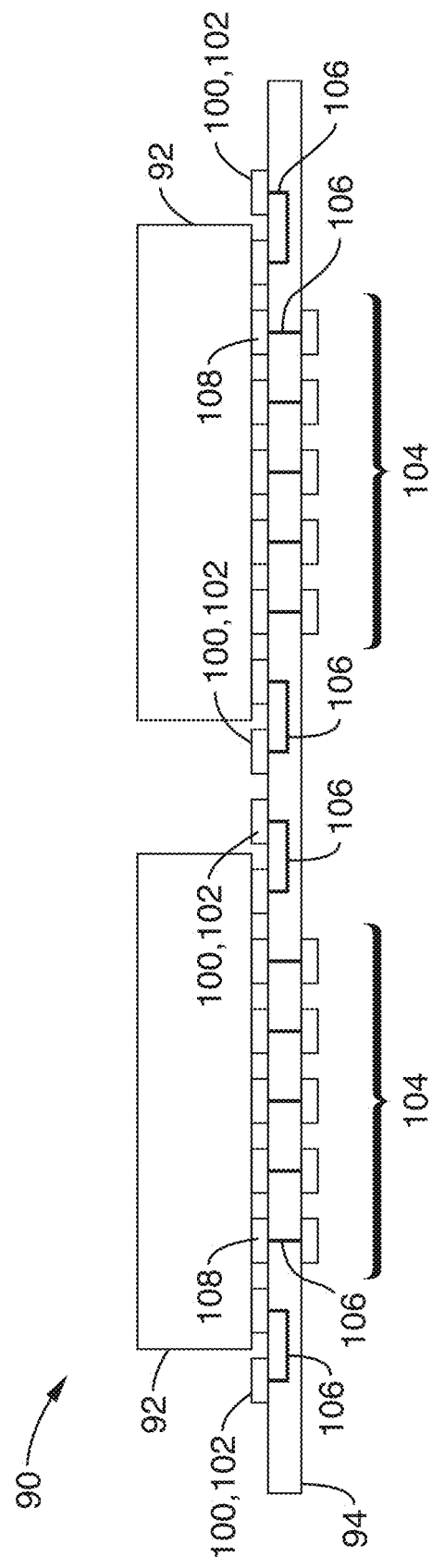

FIG. 21 is a side view of an electrode array integrated according to an embodiment of the disclosed technology, showing data and control routed about the periphery of active circuits as seen in FIG. 19.

Figure 22:
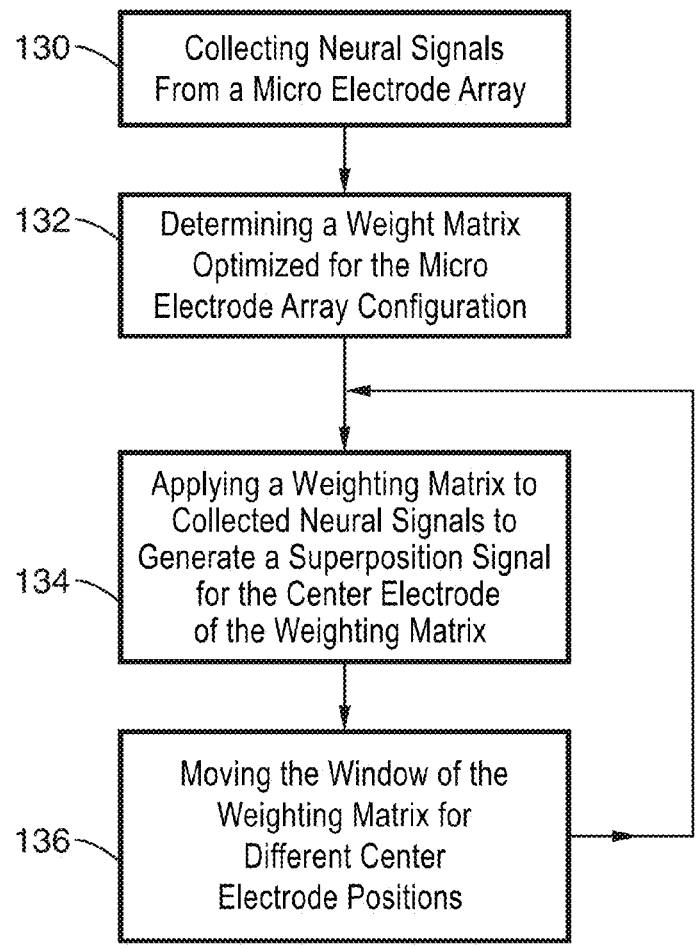

FIG. 22 is a flow diagram of applying an optimal weighting matrix in a moving window across the electrode positions of a micro electrode array according to an embodiment of the disclosed technology.

Figure 23:
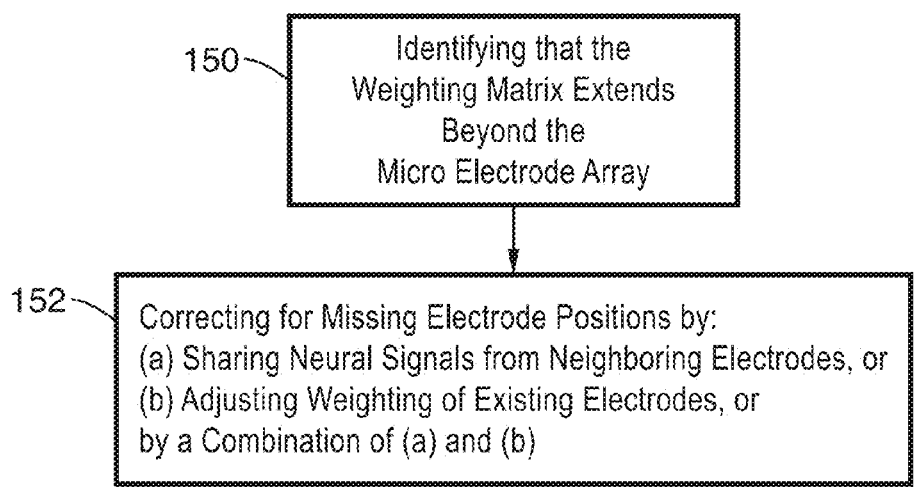

FIG. 23 is a flow diagram of correcting the weighting matrix near a boundary of the micro electrode array according to an embodiment of the disclosed technology.

DETAILED DESCRIPTION

1. Introduction

A micro electrode array apparatus and method is presented which achieves high spatial resolution for neural sensing and stimulation. Prior approaches which directly use dense electrode arrays for large channel-count neural sensing can suffer from a high mutual signal occurrence in adjacent electrodes due to low spatial resolution. Certain existing systems utilize concentric ring electrodes to enhance spatial resolution either for recording or stimulation, however, these cannot readily meet the requirements of high density electrode arrays as each ring electrode is bulky.

The technology presented herein utilizes a discrete surface Laplacian, such as are known in the art, and in the article by Disselhorst-klug, C., Silny, J. and Rau, G., entitled "Improvement of spatial resolution in surface-EMG: a theoretical and experimental comparison of different spatial filters," (IEEE Transactions on Biomedical Engineering, vol. 44, no. 7, pp. 567-574, July 1997). The Laplacian is utilized in an optimized weighting selection for the electrode array, and provides adjustable spatial resolution of each electrode for neural recording (EEG, ECoG, EMG, ECG, neural spikes), and arbitrary (selectable) current density distribution for neural stimulation applications. It will be appreciated that the Laplacian is a differential operator given by the divergence of the gradient of a function in Euclidean space. The Laplacian operator is therefore applied on the spatially distributed potentials with beneficial spatial resolution enhancement.

The technology presented can be applied on either existing commercial neural electrode arrays or implemented as a design for a specific application, and can also be extended from two-dimensional to three-dimensional arrays for full volume mapping.

Compared to prior approaches, the presented technology yields several features for use in microelectrode arrays. An optimized moving-window operator is selected for use with the microelectrode array in response to different conditions. In optimizing the moving window operator, the electrode size, pitch between electrodes, property of mediate tissue, signal source depth (EEG or ECoG), and desired spatial resolution all impact system design. Compared to a ring structure, this present technology benefits by reusing adjacent electrodes, can be applied in high-density arrays, and is not limited by electrode-shape restrictions. The disclosed technology utilizes optimized weighting based on maximizing the signal underneath the electrode and minimizing the signal from out-of-the-electrode area, thereby increasing signal-to-noise ratio. In this instance, noise is defined as the signal that comes from a surrounding region about the electrode, instead of underneath the electrode. The presented microelectrode array can also provide arbitrary (selectable) voltage distribution and current density for stimulation by controlling the stimulation weighting.

2. Focused Recording

When a disk electrode is placed onto certain target tissue for recording, it collects the signal from the signal source within a certain depth under the electrode. For EEG recording, the neural signal comes from the cortex in gray matter and will travel through cerebrospinal fluid (CSF), dura, skull, scalp all the way to the electrode. For ECoG recording, the electrodes are placed onto the dura and therefore have shorter travelling distances. Not only can the signal coming from underneath the electrode be collected, but also signal sources in surrounding electrode neighbors will contribute to the electrode. For a dipole model signal source, the recorded electrical potential is given by the following:

$$\phi = \sum_{i=1}^{N} (1/2\pi\sigma)(r_p - r_i) \cdot p_i / |r_p - r_i|^3$$

where $r_p$ represents observation point on the body surface, $r_i$ and $p_i$ represent the location and moment of the i-th primary dipole, and $\sigma$ is conductivity.

A simplified signal source model assumes that the signal sources were randomly distributed on a source plane, and electrodes were placed above the source plane with sufficient distance for signal acquisition. Based on this signal source model a recorded signal power-spatial distribution is provided for every single electrode.

Figure 1:
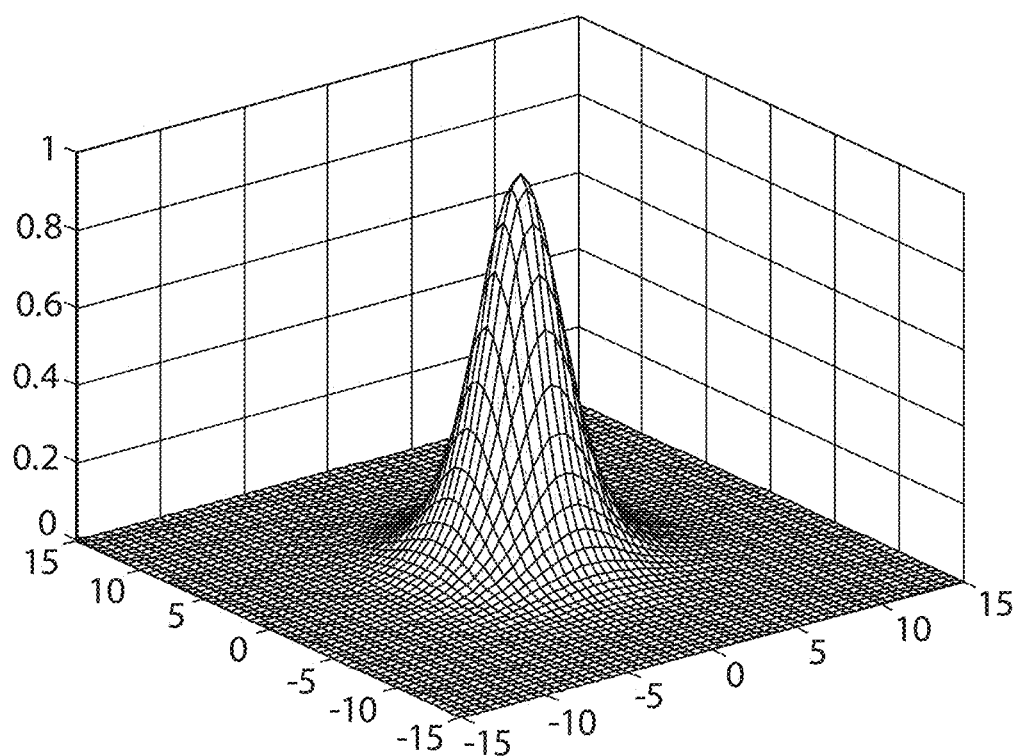
FIG. 1 is a 3D plot of normalized signal power distribution for a predetermined electrode diameter for ECoG recording.

FIG. 1 depicts a simulation result of normalized recording signal power-spatial distribution for a disk (circular) electrode, such as is utilized in ECoG recording. The signal source farther away from the electrode center contributes less signal power. In the figure, one sees a single electrode peak at location 0, 0, which slopes off rapidly.

Figure 2:
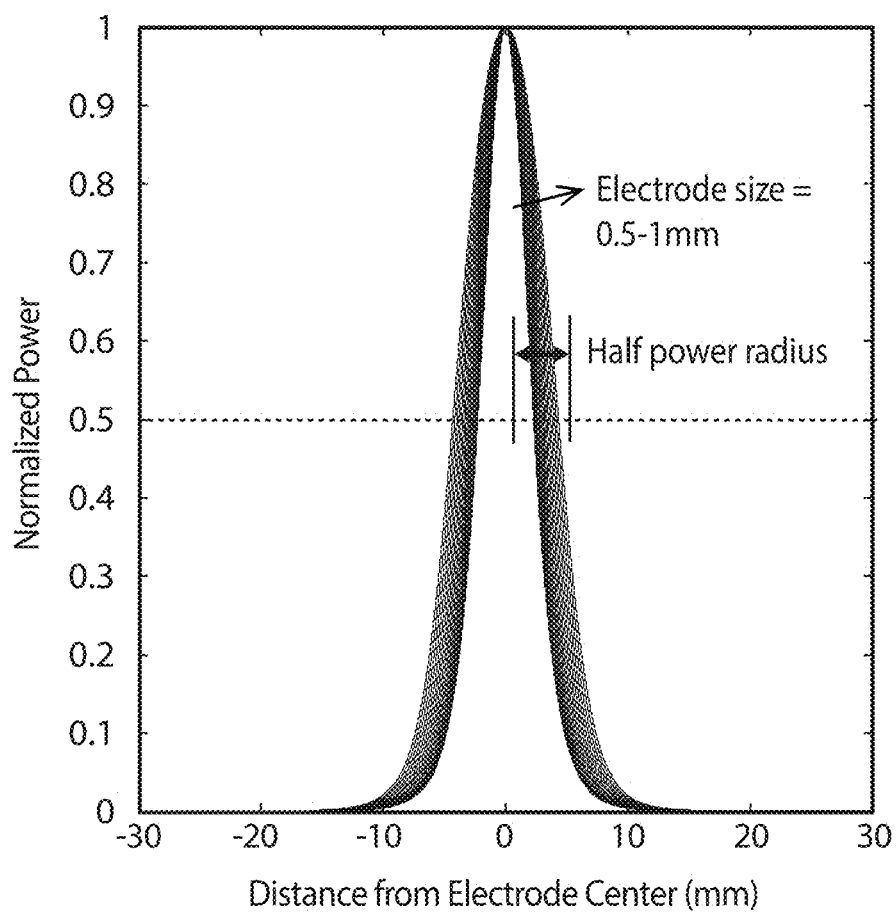
FIG. 2 is a 2D plot of power distribution for varied electrode sizes in ECoG recording.

FIG. 2 depicts a half power radius (HPR), which is defined so that the recorded signal source in the circular area with HPR from electrode center can provide more than half of the normalized maximal power. By way of example and not limitation, the disk electrode diameter in this example is in the range of 0.5 mm to about 1.0 mm, with an example tissue thickness of 4.5 mm. The circular area with HPR also denotes the −3 dB boundary. The figure also indicates the calculated HPR versus varied electrode diameter. Smaller electrode size can provide smaller HPR, which means providing a smaller spatial resolution between electrodes. Generally speaking, the concept of using a decreasing electrode size as array density increases is correct; however, there is a limitation.

FIG. 3 illustrates HPR for various electrode sizes (e.g., 0.1, 0.5, 1.0, 2.0, 3.0, 4.0, 5.0, 6.0, 7.0, 8.0, 9.0, 10.0 mm), with different signal source depths. The signal depth for EEG and ECoG is about 20 mm and 4-4.5 mm on average. For EEG and ECoG recording, the smallest half power radius is not smaller than about 9 mm and 2.2 mm, respectively.

When using an electrode array for high density recordings, every adjacent electrode can record reduplicated signals from its neighborhood.

FIG. 4A and FIG. 4B illustrate normalized power distribution for a 1 mm electrode diameter and 1.8 mm in pitch (electrode center-to-center). Center shading denotes locations inside the half power radius area. From FIG. 4A, it is clear that the recorded signals are mixed together in adjacent electrodes when pitch between electrodes is small. In the 3D depiction of FIG. 4B, the separation at the peaks and their relationships can be seen.

In this description of performing a weighting matrix, an operator matrix w is applied to (utilized upon) the recorded signal from an electrode array to produce a focused recording result. The operator itself is a weighting matrix applied onto the electrode array. Different levels of operators can be utilized, which are exemplified below, by way of example and not limitation.

$$w_{bi} = \begin{bmatrix} 0 & W_2 & 0 \\ W_5 & W_1 & W_3 \\ 0 & W_4 & 0 \end{bmatrix} \quad \text{(Bipolar)}$$

$$w_{tri} = \begin{bmatrix} 0 & 0 & W_6 & 0 & 0 \\ 0 & W_{13} & W_2 & W_7 & 0 \\ W_{12} & W_5 & W_1 & W_3 & W_8 \\ 0 & W_{11} & W_4 & W_9 & 0 \\ 0 & 0 & W_{10} & 0 & 0 \end{bmatrix} \quad \text{(Tripolar)}$$

-continued $$w_{qua} = \begin{bmatrix} 0 & 0 & 0 & W_{14} & 0 & 0 & 0 \\ 0 & 0 & W_{25} & W_6 & W_{15} & 0 & 0 \\ 0 & W_{24} & W_{13} & W_2 & W_7 & W_{16} & 0 \\ W_{23} & W_{12} & W_5 & W_1 & W_3 & W_8 & W_{17} \\ 0 & W_{22} & W_{11} & W_4 & W_9 & W_{18} & 0 \\ 0 & 0 & W_{21} & W_{10} & W_{19} & 0 & 0 \\ 0 & 0 & 0 & W_{20} & 0 & 0 & 0 \end{bmatrix} \quad \text{(Quadripolar)}$$

In the example operator pattern descriptions above, it will be appreciated that the bipolar pattern contains a center electrode and a single neighbor electrode in each of the horizontal and vertical directions, whereby it is termed bipolar. The tripolar pattern contains a center electrode and two neighbor electrodes in each of the horizontal and vertical directions, as well as a single neighbor electrode in each of the diagonal directions. The quadripolar pattern contains a center electrode and three neighboring electrodes in each of the horizontal and vertical directions, as well as two neighbor electrodes in each of the diagonal directions.

For a 5×5 Tripolar operator, the weighting matrix is applied onto the related 13 signals from 13 electrodes and results in a superposition signal for the center electrode:

$$v_1 = \sum_{i=1}^{13} W_i S_i$$

where $S_i$ denotes the recording signal from related electrode. Ideally, the use of higher operator levels can provide recording signal results with increased focus. The optimal weighting matrix w is determined by maximizing the ratio of the signal power over noise power, which is a function of weighting matrix w:

$$F(w) = \frac{\text{Signal Power } (w)}{\text{Noise Power } (w)}$$

FIG. 5 illustrates the method 10 by which signal power and noise power are generally defined in the presented technology. Signal power 16 is defined as signals arising from underneath 14 the electrode area 12, while noise power is considered to be the signal portions 18 outside of electrode area 14. It should be appreciated that variations of the present invention can be readily implemented in which area 14 can be slightly larger or smaller than the spatial extent of electrode 12, without departing from the teachings of the invention.

FIG. 6A through FIG. 6C illustrate an embodiment 30 of the disclosed technology in which the weighting matrix operates as a moving window. For the sake of simplicity of illustration, and not limitation, the section of the electrode array depicted spans only 8 rows (e.g., rows a through f) and 10 columns (e.g., columns 1 through 10). In the figure a tripolar weighting matrix (e.g., 5 electrodes wide and high) is seen centered at c3 in FIG. 6A, which moves to a center of c4 in FIG. 6B, and then to c5 in FIG. 6C.

When applying such a weighting matrix into an existing electrode array, a problem can arise if electrodes are 'missing' (outside of available physical electrode positions) at the periphery (e.g., near the edge) of the array. The present disclosure provides a method for correcting the weighting being performed.

FIG. 7A through FIG. 7C illustrate variations of an embodiment 50 for applying the weighting matrix on the electrode corner (or edge), where no electrodes exist outside of electrode block 52. Upon identifying the situation, a number of corrective actions can be taken. In FIG. 7A the missing electrodes are compensated with vicinal (i.e., in the vicinity of) electrodes. In particular, it is seen that for the tripolar weighting centered on electrode 1, electrode 1 from the electrode array is shared vertically and horizontally at a depth of two and diagonally at a depth of one, while electrode 2 is shared vertically at a depth of one, and electrode 10 is shared horizontally at a depth of one to thus fill the quadripolar pattern. In FIG. 7B the missing electrodes are discarded "x", and weighting is shared with the existing electrodes. For example, electrode 2 and electrode 10 have a doubled weighting factor. A complementary method is seen in FIG. 7C, which combines the above techniques, whereby far away missing electrodes are discarded and the weighting is shared on remaining electrodes. In the example figure, one can see that electrode 1 is shared horizontally and vertically to a depth of one, electrode 10 is shared horizontally to a depth of one, electrode 2 is shared vertically to a depth of one, while the remaining missing electrode positions are discarded. It should be appreciated that the cases of edges can be defined as degenerate cases of the corner examples, whereas the operations are carried out for only the horizontal or vertical directions in relation to neighboring electrodes.

FIG. 8A and FIG. 8B are an example of applying the optimal weighting matrix of an embodiment of this disclosure on the recorded signal from the original electrode signal described for FIG. 4A and FIG. 4B, having an electrode diameter of 1 mm and having a pitch of 1.8 mm. The original signal power is shown in FIG. 8A, and is then seen after performing the optimal weighting matrix in FIG. 8B. After applying the optimal weighting matrix, the calculated half power radius is 0.93 mm, which is approximately equal to half of the pitch. In this case, the −3 dB boundary area of recorded power distribution from the electrode is tightly leaning against the −3 dB boundary of neighborhood electrodes.

FIG. 9A and FIG. 9B depict a result of applying an example embodiment of the disclosed optimal weighting matrix onto an electrode array, having 1 mm electrode diameter and 1 mm pitch. The original signal power is shown in FIG. 9A, and is then seen after performing the optimal weighting matrix in FIG. 9B. It should be appreciated that the technology presented is configured for generating different optimal weighting matrices for different electrode configurations, such as based on parameters of electrode size and pitch, and which may also include one or more parameters of signal source depth, medium characteristics (e.g., conductivity of mediate tissue), and desired spatial resolution. It should be appreciated that half power radius is one mechanism that may be utilized as a measurement of spatial resolution, although the present disclosure is not limited in terms of spatial resolution methods.

The calculated half power radius for the figure is 0.79 mm, which is larger than half of the pitch. In this case, the recorded signal information from adjacent electrodes is therefore slightly overlapped. Signal information in this case is mixed from adjacent electrodes being recorded, whereas for certain applications it may be desirable to perform additional signal processing to distinguish the interesting information from the recorded data. Another possible case is when the half power radius is smaller than half of the pitch. In this case, signal information can be missed between adjacent electrodes.

FIG. 10 and FIG. 11 depict simulation results for applying the presently disclosed optical weighting matrix for EEG, and ECoG, respectively, at electrode sizes ranging from 1 mm through to 10 mm. In each plot the electrode center-to-center distance is shown in the horizontal axis, with half-power radius depicted in the vertical. Plots for the original electrode are seen in the upper part of each figure giving horizontal plot line results. Plots for a tripolar weighting matrix are seen in the lower (diagonal) plots. The plots show that recorded power distribution varies with electrode size, pitch between electrodes, depth of signal source, and medium conductivity. For EEG and ECoG recording, which are two of the most utilized methods for brain activity observation, overall simulation of optimal half power radius for different combinations of electrode size and pitch are seen. A dashed line is seen through the plot illustrating where the half power radius is equal to half of the pitch between electrodes. The series of numbers (i.e., 50+, 100+, 250+, 500+, 750+, 1000+ and 2000+) denote the possible maximal electrodes used to cover the half area of full head. This number is obtained for this example by calculating the maximal area occupied by an electrode for certain size of electrode array, although other approaches may be selected without departing from the teaching of the technology presented. For example, if it is desired that 100 electrodes cover the area of half of the head, then the maximal pitch between two electrodes cannot exceed 21 mm. For the case where the half power radius is to be equal to half of the pitch, the head is fully covered in this −3 dB recording power range without mixing signal information in adjacent electrodes.

For EEG recording in the case of half power radius equal to half of the pitch, the value for the maximal number of achievable original disk electrodes reaches 130 electrodes when electrode size is smaller than 6 mm with an 18 mm pitch, while the optimal-weighted electrode can have 900 electrodes when electrode size smaller than 7 mm with 7 mm of pitch. In this case, the spatial resolution is improved by 6.9 times. The minimal half power radius is 2.6 mm and 0.64 mm for EEG and ECoG, which implies a maximal number of 1653 and 27282 electrodes to cover the area of half of the head. It should be recognized that with 2.6 mm and 0.64 mm of half power radius in EEG and ECoG, respectively, information is overlapped in adjacent electrodes for the recording means.

FIG. 12 illustrates an example of extending the surface electrode array to a three dimensional array by using the tripolar weighting matrix. The focused three dimensional recording can be used with a three dimensional electrode array. The dashed arrow lines oriented in the z-direction denote penetrated probes. In this figure, 25 probes are shown with 5 electrodes on each probe, by way of example and not limitation, as with the 2D case any number of electrodes may be utilized. For a three dimensional tripolar weighting matrix, a total of 25 weighting factors are applied to the associated 25 electrode signals.

3. Focused Stimulation

FIG. 13 illustrates an example embodiment 70 of an electrode array in a modular configuration built upon the use of sub-array circuits 72 (stimulation units). The original disk electrodes are divided into n by n small electrodes 74 (e.g., 5×5 electrodes in the figure), within each of the stimulation units. When recording, the n by n electrodes are lumped together as the original disk electrodes.

It should be appreciated that the division into electrodes can also be of an n by m nature, wherein the number of rows n, need not be equal to the number of columns m. However, it should be recognized that the n×n division can be advantageous in certain applications toward simplifying control and processing of the moving window and weighting matrix. This square or rectangular electrode array pattern is preferred for many applications, as it allows the closest packaging of square, or rectangular sub-array electrodes, into a single composite electrode array.

However, it should be noted that the array pattern is not limited to a square or rectangular pattern (e.g., row and column), as the present teachings are applicable with minor modification to other array patterns (e.g., triangular, hexagonal, octagonal, circular, polar, etc.), which are in either two dimensions (2D) or three dimensions (3D), and any desired combinations thereof. The matrix processing modifications for moving from a square or rectangular pattern to other geometries will be known to one of ordinary skill in the art.

In the case where sub-array circuits are configured to provide neural stimulation, then different weighting is applied on small electrodes of a stimulation unit when performing neural stimulation to provide different current density shaping. Different weighting is shown by way of example, and not limitation, in the figure as unshaded electrodes 76, a first shading of electrodes 78, and a second shading of electrodes 80. When a voltage drop is applied on the electrode, the voltage distribution in the tissue medium can be solved by Laplace's equation. The electrical field then can be found by calculating the gradient of the voltage distribution. The current density J equals the conductivity multiplied by the electrical field. In the figure, an example of a moving window 82 is shown for use with the optimal weighting matrix.

It will be appreciated that the pattern of neural stimulation that can be applied according to FIG. 13 is not limited to the shading pattern depicted therein, but may be configured to have any desired pattern within a given sub-array circuit, which can interoperate with other sub-array circuits to provide any desired pattern for the entire array.

FIG. 14A through FIG. 14C illustrate the voltage and current density distribution of a circular electrode with 1 mm diameter, which is not subject to the optimal weighting for neural stimulation. It is well understood that the current is concentrated at the edge and causes non-uniform stimulation properties. Also, the effective stimulation area is significantly larger than the electrode area, whereby the stimulation current from one disk electrode can affect the area which underlies adjacent electrodes in a dense electrode array.

FIG. 15A through FIG. 15C illustrates voltage and current density distribution of a circular electrode with 1 mm diameter, in response to using the optimal weighting for neural stimulation. For the sake of illustrative example, the electrode is divided into 10 by 10 electrodes with certain weighting on each small electrode to perform a uniform current density distribution. It should be understood that all the voltage and current intensity of FIG. 15A on through to FIG. 18C were normalized with the same factor as that of FIG. 14A through FIG. 14C. As can be seen from FIG. 15B and FIG. 15C, the uniformity of current density distribution is increased over that seen in FIG. 14B and FIG. 14C.

FIG. 16A through FIG. 16C illustrates voltage and current density distribution of a circular electrode with 1 mm diameter, in response to using the optimal weighting for neural stimulation. In the figure, a focused current density distribution was generated by controlling the weighting of each divided small electrodes. In this case the current density can be controlled to be focused beneath the electrode range.

FIG. 17A through FIG. 17C as well as FIG. 18A through FIG. 18C illustrate examples of an arbitrarily controlled current density distribution to provide a tri-spot (FIG. 17A through FIG. 17C) or single-spot (FIG. 18A through FIG. 18C) underneath the stimulating electrode area.

4. Integration with Active Circuit

To provide for controlling the recording and stimulation of each electrode in an efficient manner with a minimum overhead of wire routing, a method for system level integration is utilized according to at least one embodiment of the present technology.

FIG. 19 illustrates an example embodiment 90 of a neural recording/stimulation apparatus shown with sub-array circuits 92, for attachment to an electrode array substrate 94, divided into sub-array blocks 96 each providing electrical connectivity to a plurality of electrodes 98 (i.e., the figure depicts 5×5 electrodes in each block). It will be appreciated that the same technique can be utilized in fabricating an array which is limited to neural sensing, or one that is limited to neural stimulation, in response to configuring the sub-array circuit to be limited to that operation. In addition substrate 94 can be populated with sub-array circuits which can provide different properties, for example utilizing sub-array circuits limited to either sensing or stimulation in different areas of the substrate, and optionally using sub-array blocks configured for both recording and stimulation in other areas.

For the sake of simplicity of illustration, FIG. 19 depicts only one circuit 92 being placed on the substrate, although each of the sub-array blocks 96 in apparatus 90 would be preferably populated with a sub-array circuit. It will be appreciated, however, that array shapes and populating them with circuits can be altered for use in specific applications without departing from the teachings hereof. For example, circuit locations (spots) can be left unpopulated so that other devices may be placed, or large through holes made for routing wiring or other elements that need pass through the interior of the substrate, and so forth.

So in general, the neural recording/stimulation apparatus comprises an active circuit chip bonded onto the corresponding location of each electrode (backside of the electrode array). Separately bonded chips on the electrode array can still provide a certain level of structure flexibility. It should be appreciated that this method can also be utilized to fabricate an electrode array on a rigid substrate, for example a silicon wafer or portion thereof.

FIG. 20 illustrates utilizing a data bus 100 and control bus 102 for providing connection of each of these circuit chips 92 on substrate 94 of the neural recording/stimulation apparatus. In at least one preferred embodiment, each circuit chip has its own identification code (e.g., number) which provides a means by which external circuitry can individually access each of the circuit chips 92. For example, each chip may incorporate a unique ID code, such as within memory, cut/etched trace maps, and so forth. In at least one embodiment, each chip outputs one channel signal at a given time while recording, although recording from all the channels can still be performed by multiplexing from one to another, since the sampling rate necessary for a given channel is generally sufficiently low. The weighting matrix is then applied onto certain channels for focused recording.

It should be appreciated that the apparatus for performing focused recording and stimulation electrode array techniques is preferably controlled in response to control circuitry 110. One of ordinary skill in the art will appreciate that this control circuitry can be implemented utilizing a range of techniques, including one or more computer processors 112 and associated memory 114, and/or other circuitry including combination of integrated circuits and discrete components, logic/gate arrays, application specific integrated circuits (ASICs), and so forth and any combination thereof. In at least one embodiment, each of the sub-array circuits 92, also contains a computer processor and memory for performing some portion of the processing of neural activity registration and/or stimulation, while being controlled by another computer processor, such as controller 110.

In at least one embodiment of the presented technology, the methods for performing the moving window and optimal weighting matrix are executed by programming retained in a memory 114, that executes on a processor 112. It will be appreciated that programming stored on memory 114, which includes solid state memory and computer-readable media, is executable on computer processor 112. The present invention is non-limiting with regard to memory and computer-readable media, insofar as these are non-transitory, and thus not constituting a transitory electronic signal.

It should be appreciated that one or more computers or processors can be utilized in real time with the presently disclosed neural electrode system to determine the optimal weighting matrix, such as based on properties including electrode size, pitch and optionally signal source depth, medium properties, and so forth. In at least one embodiment, these actions may comprise an 'online' sort of operation, or a 'hardware' implementation. It will also be recognized that for an existing electrode array, the optimal weighting matrix can be determined after the neural signal has been recorded (digitized). The optimal weighting matrix in this case can serve as an operator on the recorded (stored) signal data to gain spatial resolution improvements and/or to provide adjustable spatial resolution. Accordingly, this form of action generally comprises a form of 'offline' operation, or a 'software' implementation. According to at least one other embodiment, operation of the proposed focused electrode can also be any desired combination of the above 'online' and 'offline' forms of processing. For example, after the hardware or online processing, the processed and stored data can be further processed offline or software method to re-adjust the desired spatial resolution.

FIG. 21 illustrates the neural recording/stimulation apparatus 90, showing circuits 92 bonded to electrode array substrate 94 through contact pads 108, or other mechanisms for interconnection. In this side cross-section view, one can see how the circuit 92 is connected to the traces 106 of substrate 94 and to the electrodes 104 as well as to the data and control busses 100, 102.

FIG. 22 illustrates an example embodiment of using the optimal weighting matrix in the moving window. Neural signals are collected 130 from a micro electrode array. A weighting matrix is determined 132, or has been predetermined prior to collection of signals, for the specific micro electrode array. It will be appreciated that the weighting matrix is optimized for at least the electrode size and the electrode pitch, and more preferably to also include one or more of: mediate tissue property, signal source depth (EEG or ECoG), and desired spatial resolution. This weighting matrix, which spans a number of electrode positions in the array according to the pattern of the matrix, is applied 134 to the collected neural signals to generate a superposition signal for the center electrode of the weighting matrix. The window of the weighting matrix is then moved 136 to another center electrode position, and then the weighting matrix is applied again as per block 134. This process of applying the weighting matrix and moving the window repeats until a superposition signal has been generated for all the desired electrode positions in the micro electrode array, and is then periodically repeated to update the neural recording at each electrode position.

FIG. 23 illustrates an example embodiment of handling boundaries of the weighting matrix for an electrode array. It is first identified 150 that the weighting matrix extends outside of the electrode array. It will be noted that the center electrode of the weighting matrix always remains within the bounds of the electrodes which exist within the electrode array. A correction is then made 152 for 'missing' electrodes, which comprise those electrodes which would have been there if the weighting matrix were being applied closer to the center of the electrode array and not at the boundary of the electrode array. The correction is performed in at least one embodiment in response to: (a) sharing of electrode signals from neighboring electrodes which exist in the array, or (b) adjusting the weighting of existing electrodes, or using a combination of (a) and (b).

5. Application Examples

The focused recording and stimulation electrode array of the present disclosure can be applied in a number of different ways, the following being provided by way of example and not limitation.

5.1 Post process: The focused recording and stimulation electrode array techniques described can be utilized with existing electrode arrays (e.g., AD-TECH electrodes, or any two or three dimensional arrays). For an existing electrode array with fixed electrode size and pitch, the teachings herein provide a method to find an optimized moving weighting matrix for certain applications, including EEG or ECoG as described, to reduce the coupled/overlapped information in adjacent electrodes and therefore improve the spatial selectivity and spatial resolution of the electrode array. Additionally, the half power radius can be customized to choose the range relationship between original disk electrodes to optimized weighting matrix.

5.2 Embedded process: The focused recording and stimulation electrode array techniques described can be utilized in any new designs, that can be directed to any desired application.

The disclosed technology provides a method to determine a weighting matrix optimized for at least electrode size and pitch, for meeting a desired recording area of the target, required electrode density, and level of overlapped signal information in adjacent electrodes. By dividing the recording electrode into small electrodes, a mechanism is provided to perform uniform or arbitrary distributed current density in the medium under the electrode array.

5.3 Stimulation-only or recording-only electrode: The focused recording and stimulation electrode array techniques described herein, may also be utilized in either a stimulation-only electrode array or a recording-only electrode array.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or can be stored remotely such as on a server, or all or a portion of the programming can be stored locally and remotely. Programming stored remotely can be downloaded (pushed) to the device by user initiation, or automatically based on one or more factors. It will further be appreciated that as used herein, that the terms processor, central processing unit (CPU), and computer are used synonymously to denote a device capable of executing the programming and communication with input/output interfaces and/or peripheral devices.

From the description herein, it will be appreciated that that the present disclosure encompasses multiple embodiments which include, but are not limited to, the following:

1. An apparatus for registering neural activity, comprising: (a) a micro electrode array configured for application to a target tissue area for which neural activity is to be registered; (b) a computer processor coupled for controlling and processing signals from said micro electrode array; and (c) programming executable on the computer processor for performing steps including: (c)(i) determining a weighting matrix, which spans an area of multiple electrode positions surrounding a center electrode position, for the micro electrode array based on a given electrode configuration; (c)(ii) collecting neural signals from the micro electrode array; (c)(iii) applying the weighting matrix to a window of collected neural signals to generate a superposition signal for the center electrode and its boundary area of recording power density; (c)(iv) moving the window of the weighting matrix for different center electrode positions within the micro electrode array; and (c)(v) registering neural activity for multiple electrodes in the micro electrode array to which said weighting matrix is applied in the moving window.

2. The apparatus of any preceding embodiment, wherein said apparatus is further configured for performing neural stimulation in response to said programming which is further configured for generating neural stimulation with a selectable current density distribution controlled by stimulation weighting of the weighting matrix.

3. The apparatus of any preceding embodiment, wherein said pattern for said weighting matrix is selected from a group of patterns consisting of bipolar, tripolar, and quadripolar, each of which selects a different number of neighboring electrodes surrounding the center electrode.

4. The apparatus of any preceding embodiment, further comprising programming executable on said computer processor for optimizing selection of a moving-window operator having a desired pattern when performing a weighting matrix as a moving window.

5. The apparatus of any preceding embodiment, wherein said programming executable on the computer processor is configured for determining said boundary area based on half power radius.

6. The apparatus of any preceding embodiment, wherein said programming executable on the computer processor is configured for distinguishing signals arising from underneath an electrode as signal power, and signals outside of that region as noise power.

7. The apparatus of any preceding embodiment, wherein said programming executable on the computer processor determines electrode configurations based on electrode size and pitch.

8. The apparatus of any preceding embodiment, wherein said programming executable on the computer processor electrode additionally determines electrode configurations based on parameters of signal source depth, or medium conductivity, or a combination thereof.

9. The apparatus of any preceding embodiment, wherein said programming executable on the computer processor electrode additionally determines electrode configurations based on desired spatial resolution.

10. The apparatus of any preceding embodiment, wherein said weighting matrix is two dimensional or three dimensional.

11. The apparatus of any preceding embodiment, wherein the micro electrode array provides adjustable spatial resolution of each electrode for neural registration.

12. The apparatus of any preceding embodiment, wherein said apparatus is configured for registering neural activity as selected from a group of neural activity registration techniques consisting of EEG, ECoG, EMG, ECG, and registration of neural spikes.

13. The apparatus of any preceding embodiment, wherein the micro electrode array is configured as a two-dimensional or three-dimensional array to provide full volume mapping.

14. The apparatus of any preceding embodiment, wherein said micro electrode array comprises a plurality of sub-array circuits coupled for communication to said computer processor.

15. The apparatus of any preceding embodiment, wherein each of said sub-array circuits integrates active circuits within it for locally processing neural signals and communicating through a data and control bus with said computer processor.

16. An apparatus for registering neural activity and performing neural stimulation, comprising: (a) a micro electrode array configured for application to a target tissue area for which neural activity is to be registered; (b) a computer processor coupled for controlling and processing signals from said micro electrode array; and (c) programming executable on the computer processor for performing steps comprising: (c)(i) determining a weighting matrix, which spans an area of multiple electrode positions in a window surrounding a center electrode position, for the micro electrode array based on electrode configuration; (c)(ii) collecting neural signals from the micro electrode array; (c)(iii) applying the weighting matrix to collected neural signals to generate a superposition signal for the center electrode and its boundary area of recording power density; (c)(iv) moving the window of the weighting matrix for different center electrode positions within the micro electrode array; and (v) registering neural activity for multiple electrodes in the micro electrode array to which said weighting matrix is applied in the moving window; and (c)(vi) performing neural stimulation with a selectable current density distribution controlled by stimulation weighting of the weighting matrix.

17. The apparatus of any preceding embodiment, further comprising programming executable on said computer processor for optimizing selection of a moving-window operator having a desired pattern when performing a weighting matrix as a moving window.

18. The apparatus of any preceding embodiment, wherein said programming executable on the computer processor determines electrode configurations based on electrode size and pitch.

19. The apparatus of any preceding embodiment, wherein said programming executable on the computer processor electrode additionally determines electrode configurations based on parameters of signal source depth, or medium conductivity, or a combination thereof.

20. The apparatus of any preceding embodiment, wherein said programming executable on the computer processor electrode additionally determines electrode configurations based on desired spatial resolution.

21. The apparatus of any preceding embodiment, wherein the weighting matrix is two dimensional or three dimensional.

22. The apparatus of any preceding embodiment, wherein said apparatus is configured for registering neural activity as selected from a group of neural activity registration consisting of EEG, ECoG, EMG, ECG, and registration of neural spikes.

23. The apparatus of any preceding embodiment, wherein the micro electrode array is configured as a two-dimensional or three-dimensional array to provide full volume mapping.

24. The apparatus of any preceding embodiment, wherein said micro electrode array comprises a plurality of sub-array circuits coupled to said computer processor.

25. The apparatus of any preceding embodiment, wherein each of said sub-array circuits integrates active circuits within it for locally generating neural stimulation and processing neural signals in response to communicating through a data and control bus with said computer processor.

26. An apparatus for generating neural stimulation, comprising: (a) a micro electrode array configured for application to a target tissue area for which neural stimulation is to be provided; (b) a computer processor coupled for controlling and processing signals from said micro electrode array; and (c) programming executable on the computer processor for performing steps comprising: (c)(i) determining a weighting matrix, which spans an area of multiple electrode positions in a window surrounding a center electrode position, for the micro electrode array based on electrode configuration; (c)(ii) performing neural stimulation with a selectable current density distribution controlled by stimulation weighting of the weighting matrix; (c)(iii) moving the window of the weighting matrix for different center electrode positions within the micro electrode array; and (c)(iv) whereby in response to neural stimulation at different moving window positions stimulation is provided to multiple electrodes in the micro electrode array.

27. The apparatus of any preceding embodiment: wherein said micro electrode array comprises a plurality of sub-array circuits coupled for communication with said computer processor; wherein each of said sub-array circuits integrates active circuits within it for locally generating neural stimulation in response to communicating through a data and control bus with said computer processor.

28. A method for registering neural activity using a micro electrode array, the method comprising: (a) determining a weighting matrix, which spans multiple electrode positions in a window surrounding a center electrode position, for a micro electrode array based on electrode configuration; (b) collecting neural signals from the micro electrode array; (c) applying the weighting matrix to collected neural signals to generate a superposition signal for the center electrode and its boundary area of recording power density; (d) moving the window of the weighting matrix for different center electrode positions within the micro electrode array; and (e) registering neural activity for multiple electrodes in the micro electrode array to which said weighting matrix is applied in the moving window.

29. The method of any preceding embodiment, wherein the method further comprises performing neural stimulation while providing selectable current density distribution controlled by stimulation weighting of the weighting matrix.

30. The method of any preceding embodiment, wherein said boundary area is based on half power radius.

31. The method of any preceding embodiment, wherein signals arising from underneath an electrode are considered as signal power and evaluated, while signals outside of that region are considered as noise power and discarded.

32. The method of any preceding embodiment, wherein electrode configurations are determined in response to electrode size and electrode pitch.

33. The method of any preceding embodiment, wherein electrode configurations are further determined in response to signal source depth, or medium conductivity, or a combination thereof.

34. The method of any preceding embodiment, wherein electrode configurations are further determined in response to desired spatial resolutions.

35. The method of any preceding embodiment, wherein the weighting matrix is two dimensional or three dimensional.

36. The method of any preceding embodiment, wherein the micro electrode array provides adjustable spatial resolution of each electrode.

37. The method of any preceding embodiment, wherein registering of neural activity is selected from the group of neural activity registration consisting of EEG, ECoG, EMG, ECG, and registration of neural spikes.

38. The method of any preceding embodiment, wherein the micro electrode array is configured for use in electrode arrays of two-dimensions or three-dimensions to provide full volume mapping.

39. The method of any preceding embodiment, further comprising optimized selection of a moving-window operator when performing a weighting matrix as a moving window.

40. The method of any preceding embodiment, further comprising optimized weighting based on maximizing signal underneath an electrode and minimizing the signal from out-of-the-electrode area, thereby increasing signal-to-noise ratio.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for recording neural activity, comprising:
   (a) a micro electrode array configured for application to a target tissue area of the brain for which neural activity is to be recorded, with said micro electrode array comprising a plurality of electrodes, arranged in at least a two dimensional array, with the electrodes positioned so that recorded signal information from adjacent electrodes overlap one another;
   (b) multiple sub-array active circuits, each sub-array active circuit electrically coupled to a plurality of the electrodes of the micro electrode array and which receives data and control signals for performing recording and stimulation;
   (c) a computer processor having data and control signal lines connected to said multiple sub-array active circuits for controlling stimulation of said micro electrode array and processing signals from said micro electrode array; and
   (d) a non-transitory memory storing instructions executable by the processor;
   (e) wherein said instructions, when executed by the computer processor, perform steps comprising:
      (i) determining a weighting matrix, which spans an area of multiple electrode positions surrounding a center electrode position, for the micro electrode array based on a given electrode configuration;
      (ii) collecting neural signals from the micro electrode array;
      (iii) applying the weighting matrix to a window of collected neural signals to generate a superposition signal for the center electrode and its boundary area of recording power density;
      (iv) moving the window of the weighting matrix for different center electrode positions within the micro electrode array; and
      (v) recording neural activity for multiple electrodes in the micro electrode array to which said weighting matrix is applied in the moving window.

2. The apparatus recited in claim 1, wherein said apparatus is further configured for performing neural stimulation in response to said programming which is further configured for generating neural stimulation with a selectable current density distribution controlled by stimulation weighting of the weighting matrix.

3. The apparatus recited in claim 1, wherein said weighting matrix has a pattern selected from a group of patterns consisting of bipolar, tripolar, and quadripolar, each of which selects a different number of neighboring electrodes surrounding the center electrode.

4. The apparatus recited in claim 1, wherein said programming executable on the computer processor is configured for determining said boundary area based on half power radius.

5. The apparatus recited in claim 4, wherein said programming executable on the computer processor is configured for distinguishing signals arising from the target tissue area underneath an electrode as signal power, from signals arising outside of that region which are considered noise power.

6. The apparatus recited in claim 1, wherein said programming executable on the computer processor determines electrode configurations based on electrode size and pitch between electrodes.

7. The apparatus recited in claim 6, wherein said programming executable on the computer processor additionally determines electrode configurations based on parameters of signal source depth, or medium conductivity, or a combination thereof.

8. The apparatus recited in claim 7, wherein said programming executable on the computer processor electrode additionally determines electrode configurations based on selected spatial resolution of the micro electrode array.

9. The apparatus recited in claim 1, wherein said weighting matrix is two dimensional or three dimensional.

10. The apparatus recited in claim 1, wherein said apparatus is configured for recording neural activity as selected from a group of neural activity recording techniques consisting of EEG, ECoG, EMG, ECG, and recording of neural spikes.

11. The apparatus recited in claim 1, wherein the micro electrode array is configured as a two-dimensional or three-dimensional array to provide full volume mapping.

12. The apparatus recited in claim 1, wherein said micro electrode array comprises a plurality of sub-array circuits coupled for communication to said computer processor.

13. The apparatus recited in claim 12, wherein each of said sub-array circuits integrates active circuits within it for locally processing neural signals and communicating through a data and control bus with said computer processor.

14. An apparatus for recording neural activity and performing neural stimulation, comprising:
   (a) a micro electrode array configured for application to a target tissue area of the brain for which neural activity is to be recorded, with said micro electrode array comprising a plurality of electrodes, arranged in at least a two dimensional array, with electrodes positioned so that recorded signal information from adjacent electrodes overlap one another;

(b) multiple sub-array active circuits, each sub-array active circuit electrically coupled to a plurality of the electrodes of the micro electrode array and which receives data and control signals for performing recording and stimulation;

(c) a computer processor having data and control signal lines connected to multiple sub-array active circuits for controlling stimulation of said micro electrode array and processing signals from said micro electrode array; and (d) a non-transitory memory storing instructions executable by the processor;

(e) wherein said instructions, when executed by the computer processor, perform steps comprising:

(i) determining a weighting matrix, which spans an area of multiple electrode positions in a window surrounding a center electrode position, for the micro electrode array based on electrode configuration;

(ii) collecting neural signals from the micro electrode array;

(iii) applying the weighting matrix to collected neural signals to generate a superposition signal for the center electrode and its boundary area of recording power density;

(iv) moving the window of the weighting matrix for different center electrode positions within the micro electrode array;

(v) recording neural activity for multiple electrodes in the micro electrode array to which said weighting matrix is applied in the moving window; and (vi) performing neural stimulation with a selectable current density distribution controlled by stimulation weighting of the weighting matrix.

15. The apparatus recited in claim 14, wherein said programming executable on the computer processor is configured for optimizing selection of a moving-window operator having a desired pattern when performing a weighting matrix as a moving window.

16. The apparatus recited in claim 14, wherein said programming executable on the computer processor determines electrode configurations based on electrode size and pitch between electrodes.

17. The apparatus recited in claim 16, wherein said programming executable on the computer processor additionally determines electrode configurations based on parameters of signal source depth, or medium conductivity, or a combination thereof.

18. The apparatus recited in claim 16, wherein said programming executable on the computer processor electrode additionally determines electrode configurations based on desired spatial resolution.

19. The apparatus recited in claim 14, wherein the weighting matrix is two dimensional or three dimensional.

20. The apparatus recited in claim 14, wherein said apparatus is configured for recording neural activity as selected from a group of neural activity recording consisting of EEG, ECoG, EMG, ECG, and recording of neural spikes.

21. The apparatus recited in claim 14, wherein the micro electrode array is configured as a two-dimensional or three-dimensional array to provide full volume mapping.

22. The apparatus recited in claim 14, wherein said micro electrode array comprises a plurality of sub-array circuits coupled to said computer processor.

23. The apparatus recited in claim 22, wherein each of said sub-array circuits integrates active circuits within it for locally generating neural stimulation and processing neural signals in response to communicating through a data and control bus with said computer processor.

24. An apparatus for generating neural stimulation, comprising:

(a) a micro electrode array configured for application to a target tissue area of the brain for which neural stimulation is to be provided, with said micro electrode array comprising a plurality of electrodes, arranged in at least a two dimensional array, with the electrodes positioned so that stimulations generated from adjacent electrodes overlap one another;

(b) multiple sub-array active circuits, each sub-array active circuit electrically coupled to a plurality of the electrodes of the micro electrode array and which receives data and control signals for performing recording and stimulation;

(c) a computer processor having data and control signal lines connected to said multiple sub-array active circuits for controlling stimulation from said micro electrode array and processing signals from said micro electrode array;

(d) a non-transitory memory storing instructions executable by the processor; and (e) wherein said instructions, when executed by the computer processor, perform steps comprising:

(i) determining a weighting matrix, which spans an area of multiple electrode positions in a window surrounding a center electrode position, for the micro electrode array based on electrode configuration;

(ii) performing neural stimulation with a selectable current density distribution controlled by stimulation weighting of the weighting matrix; and (iii) moving the window of the weighting matrix for different center electrode positions within the micro electrode array;

(iv) whereby in response to neural stimulation at different moving window positions stimulation is provided to multiple electrodes in the micro electrode array.

25. The apparatus recited in claim 24:

wherein said micro electrode array comprises a plurality of sub-array circuits coupled for communication with said computer processor; and wherein each of said sub-array circuits integrates active circuits within it for locally generating neural stimulation in response to communicating through a data and control bus with said computer processor.

* * * * *